(12) United States Patent
Byun et al.

(10) Patent No.: US 10,059,743 B2
(45) Date of Patent: Aug. 28, 2018

(54) PEPTIDE DERIVATIVE FOR REGULATING THYMIC STROMAL LYMPHOID PROTEIN-MEDIATED SIGNALING AND PHARMACEUTICAL COMPOSITION FOR PREVENTING AND TREATING ALLERGY AND ASTHMA DISEASES COMPRISING SAME

(71) Applicant: KOREA UNIVERSITY RESEARCH AND BUSINESS FOUNDATION, SEJONG CAMPUS, Sejong-si (KR)

(72) Inventors: Youngjoo Byun, Daejeon (KR); Ki Yong Lee, Sejong-si (KR); Kiho Lee, Seoul (KR); Young Ho Jeon, Sejong-si (KR); Yong Woo Jung, Daejeon (KR)

(73) Assignee: KOREA UNIVERSITY RESEARCH AND BUSINESS FOUNDATION, SEJONG CAMPUS, Sejong-si (KR)

( * ) Notice: Subject to any disclaimer, the term of this patent is extended or adjusted under 35 U.S.C. 154(b) by 0 days.

(21) Appl. No.: 15/558,286

(22) PCT Filed: Mar. 10, 2016

(86) PCT No.: PCT/KR2016/002388
§ 371 (c)(1),
(2) Date: Sep. 14, 2017

(87) PCT Pub. No.: WO2016/148437
PCT Pub. Date: Sep. 22, 2016

(65) Prior Publication Data
US 2018/0148474 A1    May 31, 2018

(30) Foreign Application Priority Data

Mar. 17, 2015 (KR) ......................... 10-2015-0036723
Mar. 7, 2016 (KR) ......................... 10-2016-0026865

(51) Int. Cl.
*C07K 7/06* (2006.01)
*A61K 38/08* (2006.01)
*A61K 45/06* (2006.01)

(52) U.S. Cl.
CPC ................ *C07K 7/06* (2013.01); *A61K 38/08* (2013.01); *A61K 45/06* (2013.01)

(58) Field of Classification Search
CPC ........... A61K 38/08; A61K 45/06; C07K 7/06
See application file for complete search history.

(56) References Cited

U.S. PATENT DOCUMENTS

| 7,731,953 B2 * | 6/2010 | Leonard ............. A01K 67/0276 424/93.71 |
| 2005/0249712 A1 * | 11/2005 | Leonard ............. A01K 67/0276 424/93.71 |
| 2007/0237787 A1 | 10/2007 | Leonard et al. ........... 424/204.1 |
| 2013/0225490 A1 | 8/2013 | Sims et al. ..................... 514/7.9 |

FOREIGN PATENT DOCUMENTS

| KR | 10-2015-0006639 | 1/2015 | ........... A61K 31/122 |
| WO | WO02/099062 | * 12/2002 | |

OTHER PUBLICATIONS

Park et al. Synthesis and biological evaluation of peptide-derived TSLP inhibitors. Bioorganic & Medicinal Chemistry Letters, Sep. 7, 2017. vol. 27, pp. 4710-4713. (Year: 2017).*
International Search Report (ISR) from corresponding International Application No. PCT/KR2016/002388 dated Jul. 6, 2016 and its English translation.
Pubchem, CID 21279213, http://pubchem.ncib.nlm.nih.gov/compound/21279213, dated Dec. 5, 2007, p. 1-9.
Pubchem, CID20017944, http://pubchem.ncib.nlm.nih.gov/compound/20017944, dated Dec. 5, 2007, p. 1-9.
Bosnjak et al.; "Treatment of Allergic Asthma: Modulation of Th2 Cells and their Responses", Respiratory Research, vol. 12, Article 114, 2011, Internal pp. 1-17.
Zhang et al.: "Functions of Thymic Stromal Lymphopoietin in Immunity and Disease", Immunologic Research, Vo.. 52, No. 3, 2012, Internal pp. 1-20.

* cited by examiner

*Primary Examiner* — Marcela M Cordero Garcia
(74) *Attorney, Agent, or Firm* — Harness, Dickey & Pierce, P.L.C.

(57) ABSTRACT

The present invention relates to a peptide derivative for regulating the thymic stromal lymphoid protein-mediated signaling and a pharmaceutical composition including the peptide derivative for preventing and treating allergy and asthma diseases and, more particularly, to a peptide derivative represented by Chemical Formula 1 and a pharmaceutical composition including the peptide derivative for preventing and treating allergy and asthma diseases. According to the present invention, provided are a peptide derivative capable of effectively inhibiting the formation of an inflammatory response of allergy and asthma diseases and a pharmaceutical composition including the peptide derivative. By using the present invention, various allergy and asthma diseases can be fundamentally prevented or treated.

7 Claims, 16 Drawing Sheets

Specification includes a Sequence Listing.

PEPTIDE DERIVATIVE FOR REGULATING THYMIC STROMAL LYMPHOID PROTEIN-MEDIATED SIGNALING AND PHARMACEUTICAL COMPOSITION FOR PREVENTING AND TREATING ALLERGY AND ASTHMA DISEASES COMPRISING SAME

CROSS-REFERENCE TO RELATED APPLICATIONS

This application is a national phase application of PCT/KR2016/002388, filed on Mar. 10, 2016, which claims the benefit of priority to Korean Patent Application Nos. 10-2015-0036723 filed on Mar. 17, 2015 and 10-2016-0026865 filed on Mar. 7, 2016, the disclosures of which are incorporated herein by references.

TECHNICAL FIELD

The present invention relates to peptide derivatives for regulating thymic stromal lymphopoietin-mediated signal transduction and pharmaceutical compositions for preventing and treating allergic and asthmatic diseases containing the peptide derivatives as active ingredients.

BACKGROUND ART

Treatment of allergic inflammatory diseases with bronchodilators and anti-inflammatory agents is based on allopathy. These therapeutic agents are temporarily effective in ameliorating symptoms of allergic diseases but cannot basically control allergic diseases, failing to fundamentally treat the diseases.

In this connection, environmental diseases, such as bronchial asthma, atopic skin diseases, and allergic rhinitis, are known as immune diseases and Th2 cells are well known to play a central role in causing allergic responses. When stimulated by an antigen in lymphocytes, CD4 T cells can be differentiated into various types of Th cells depending on cytokines recognized simultaneously by the cells. When the recognized cytokines are type 2 cytokines, such as thymic stromal lymphopoietin (TSLP) or IL-4, such cells are differentiated into Th2 to cause allergic responses.

In addition, it was confirmed that dendritic cells presenting antigens to CD4 T cells also respond to stimulation by TSLP and assist in the differentiation of Th2 cells. After the differentiated Th2 cells migrate to allergy-causing tissue sites, for example, in the lung or skin, cytokines secreted from the corresponding tissues also play an important in the activation of the cells.

Such cytokines include TSLP, IL-25, and IL-33. Among these cytokines, TSLP is likely to play the most effective role. It was also found that suppression of TSLP secretion from animal models makes the formation and activation of Th2 cells difficult, causing no disease in the animals. It was also reported that suppression of TSLP in animals afflicted with diseases is helpful in treating the diseases. Overall, TSLP is an important cytokine that are involved in both differentiation and activation of Th2 cells and the regulation of TSLP is recognized to be important in the treatment of allergic diseases.

Many therapeutic approaches targeting TSLP have been reported. For example, Korean Patent Publication No. 2008-0099330 discloses antibodies which neutralize human TSLP activity and methods for the treatment of human TSLP related disorders, such as asthma, atopic dermatitis, and allergic rhinitis. Further, Korean Patent Publication No. 2009-0088950 discloses TSLP-specific antibodies and uses thereof in the treatment of allergic inflammatory disorders.

Further, Korean Patent Publication No. 2015-0006639 discloses a pharmaceutical composition having the ability to inhibit TSLP secretion which contains a compound represented by Formula 1 or a pharmaceutically acceptable salt thereof as an active ingredient.

DETAILED DESCRIPTION

Problems to be Solved by the Invention

Thus, the present invention is directed to providing peptide derivatives that regulate TSLP-mediated intracellular signal transduction to effectively inhibit intracellular phosphorylation of STAT5, thus being very effective in preventing and treating allergic and asthmatic diseases. The present invention is also directed to providing pharmaceutical compositions including the peptide derivatives.

Means for Solving the Problems

In one aspect, the present invention provides a peptide derivative represented by Formula 1:

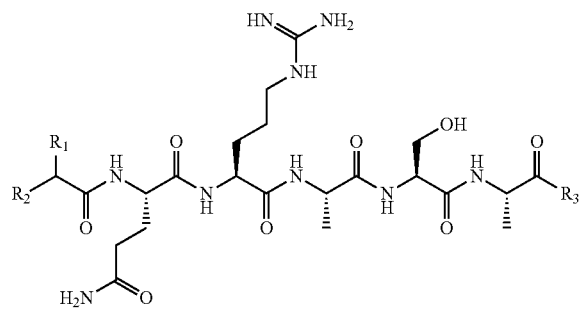

[Formula 1]

wherein $R_1$ is a guanidine-substituted $C_1$-$C_4$ alkyl group, $R_2$ is selected from an amine groups and the following structures 1:

[Structures 1]
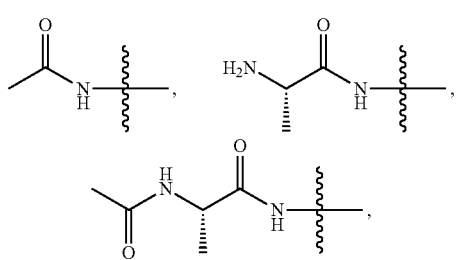
[Structure 2]
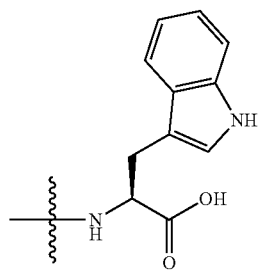
and
R₃ is selected from a hydroxyl group and the following structure 2:
According to one embodiment of the present invention, the peptide derivative of Formula 1 may be selected from those represented by Formulae 2 to 9:
[Formula 2]
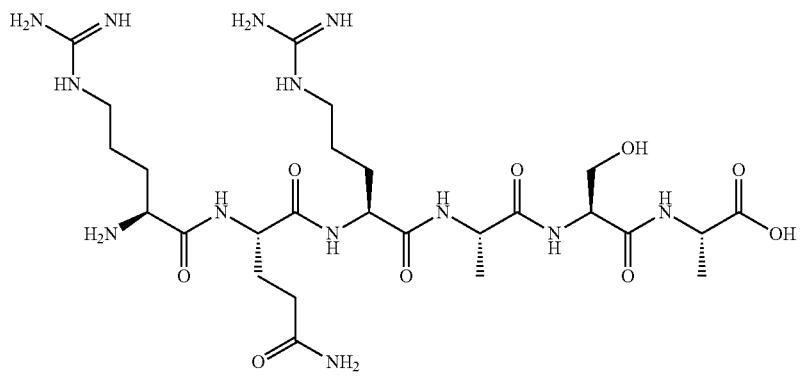
[Formula 3]
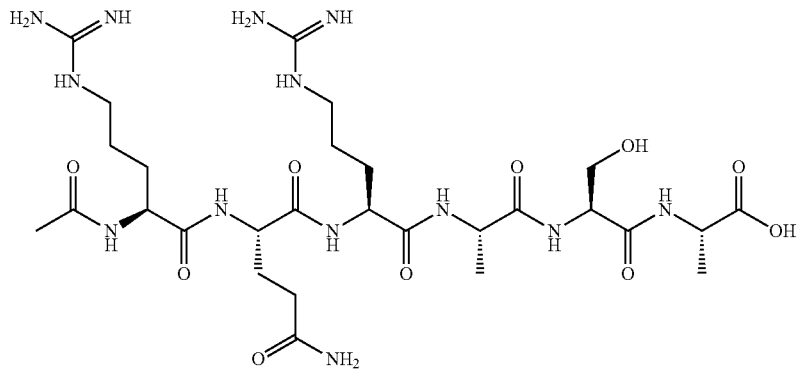
[Formula 4]
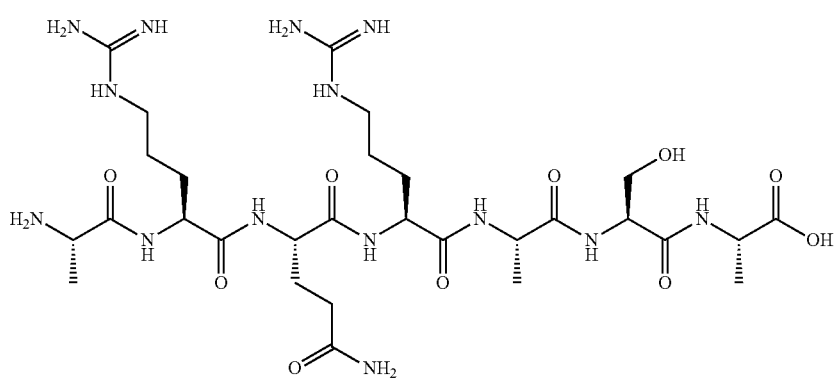

[Formula 5]
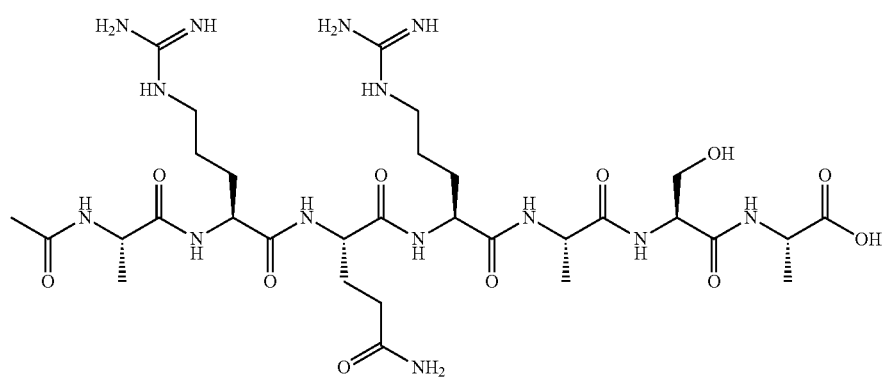
[Formula 6]
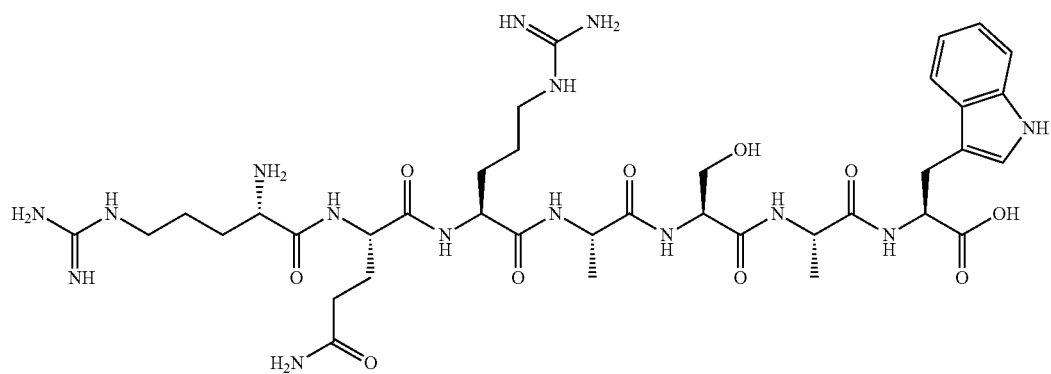
[Formula 7]
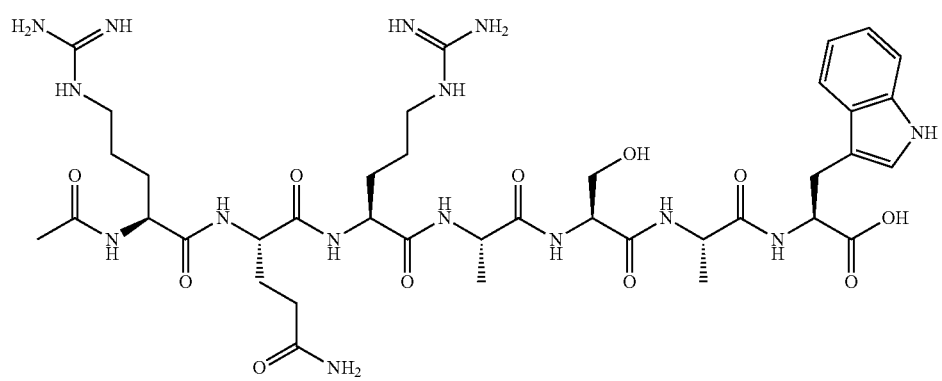
[Formula 8]
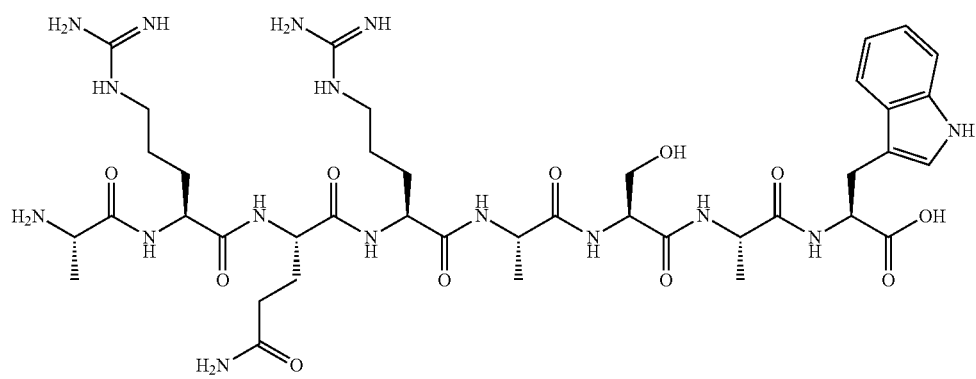

-continued

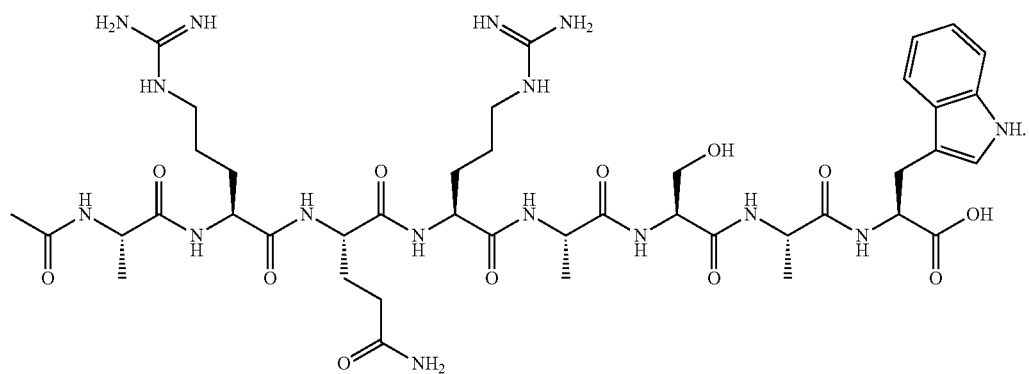

[Formula 9]

In a further aspect, the present invention provides a pharmaceutical composition for preventing and treating allergic and asthmatic diseases including the peptide derivative represented by Formula 1 or a salt thereof as an active ingredient.

According to one embodiment of the present invention, the peptide derivative of Formula 1 may be selected from those represented by Formulae 2 to 9:

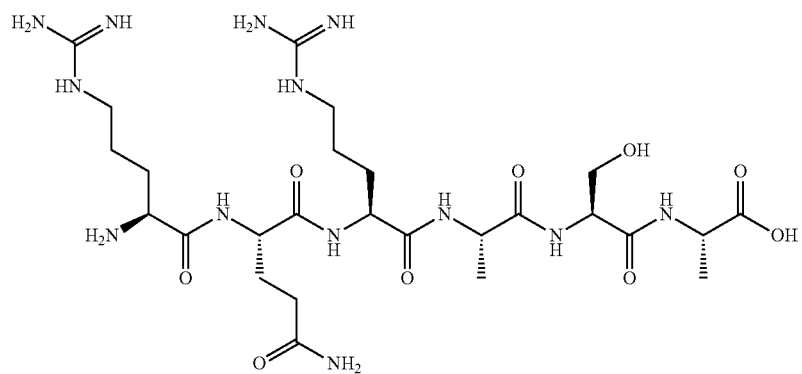

[Formula 2]

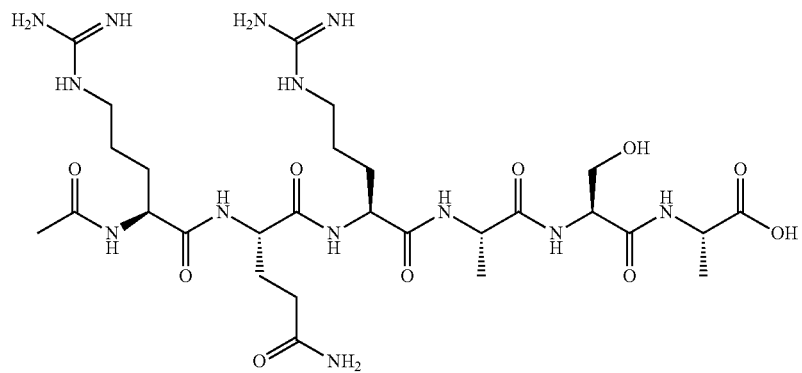

[Formula 3]

[Formula 4]
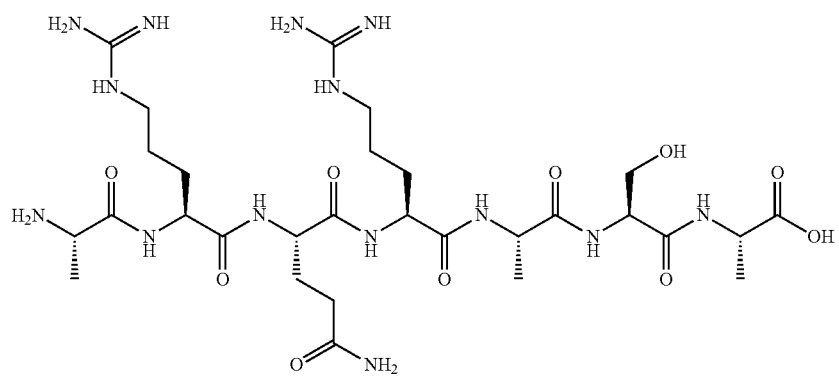
[Formula 5]
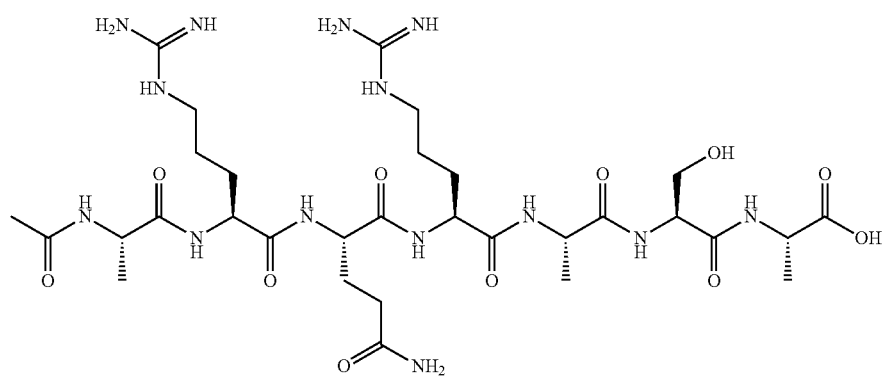
[Formula 6]
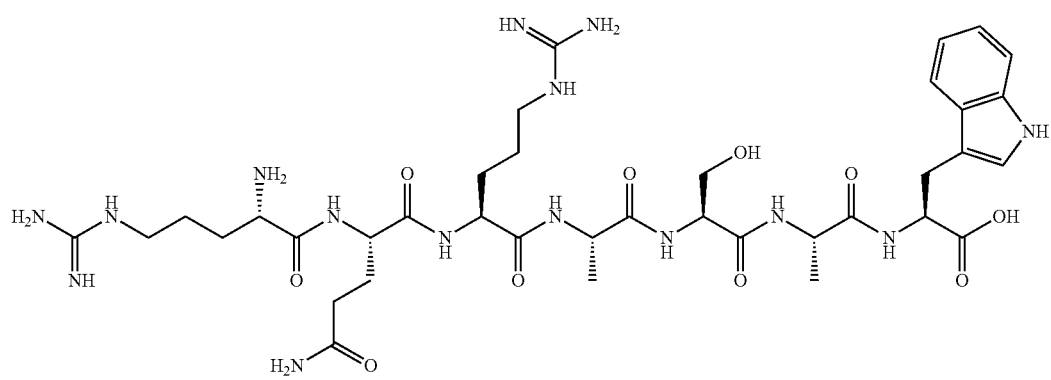
[Formula 7]
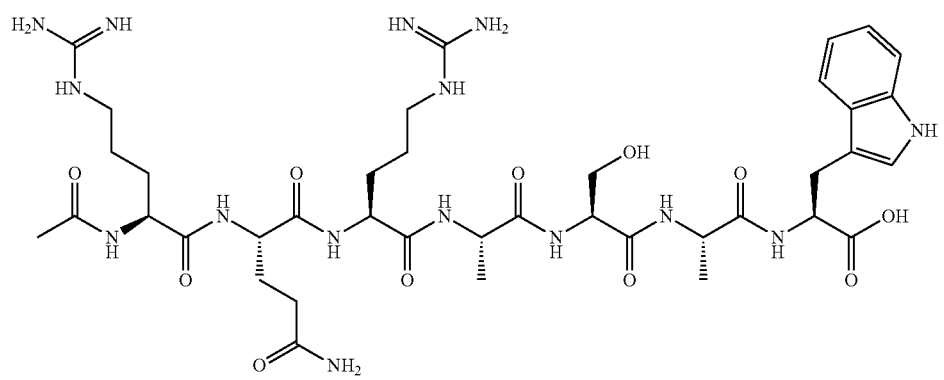

[Formula 8] (chemical structure)

[Formula 9] (chemical structure)

According to a further embodiment of the present invention, the allergic diseases may be atopic dermatitis, rash, and allergic rhinitis.

According to another embodiment of the present invention, the pharmaceutical composition may further include one or more ingredients selected from the group consisting of other drugs for preventing and treating allergic and asthmatic diseases, excipients, diluents, adjuvants, and stabilizers.

According to another embodiment of the present invention, the stabilizers may be selected from the group consisting of proteins, carbohydrates, buffers, and mixtures thereof.

Effects of the Invention

The peptide derivatives of the present invention are effective in suppressing inflammatory responses associated with allergic and asthmatic diseases. In addition, the peptide derivatives and the pharmaceutical compositions of the present invention can be used to fundamentally prevent or treat various allergic and asthmatic diseases.

BEST MODE FOR CARRYING OUT THE INVENTION

Figure 1A:
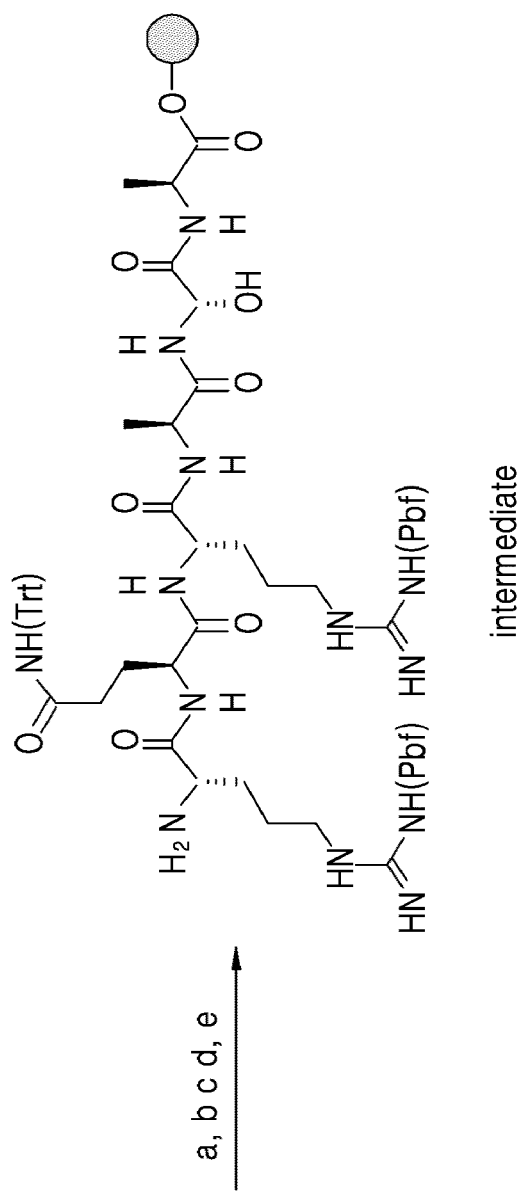
FIGS. 1a, 1b, 1c, 1d, 1e, 1f, 1g, 1h, and 1j schematically show procedures for synthesizing TSLP-binding peptide derivatives of the present invention by the solid phase method.
Figure 1A:
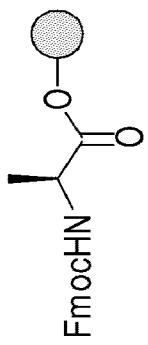

The present invention will now be described in more detail.

The present inventors have found for the first time that peptide derivatives represented by Formula 1 effectively inhibit TSLP, a key cytokine inducing asthmatic and allergic diseases, from binding to its receptor. The present invention has been accomplished based on this finding.

[Formula 1]

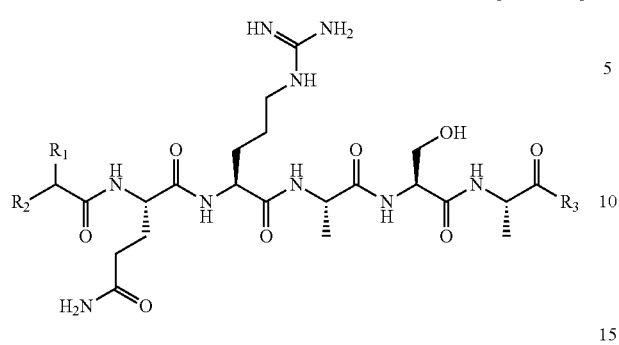

wherein $R_1$ is a guanidine-substituted $C_1$-$C_4$ alkyl group, $R_2$ is selected from an amine groups and the following structures 1:

[Structures 1]

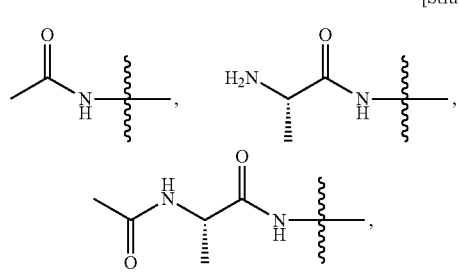

and $R_3$ is selected from a hydroxyl group and the following structure 2:

[Structure 2]

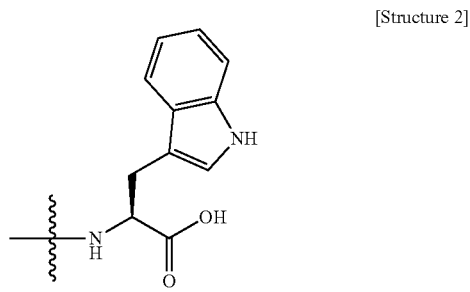 [SMILES: *N[C@@H](Cc1c[nH]c2ccccc12)C(=O)O]

The peptide derivatives represented by Formula 1 have in common the same amino acid sequence: H$_2$N-Arg-Gln-Arg-Ala-Ser-Ala-COOH (SEQ ID NO:1). The N-terminus of the amino acid sequence may be optionally substituted with other substituents or added with other amino acid residues.

The peptide derivatives of the present invention may be prepared by the solid phase method using the Fmoc-strategy. For example, in order to synthesize peptides whose C-termini are amidated, various forms of peptide derivatives may be prepared using Fmoc-Ala-Wang-resin or H$_2$N-Ala-Wang-resin as a starting material.

For example, the method may be used to prepare one of the peptide derivatives represented by Formulae 2 to 9:

[Formula 2]

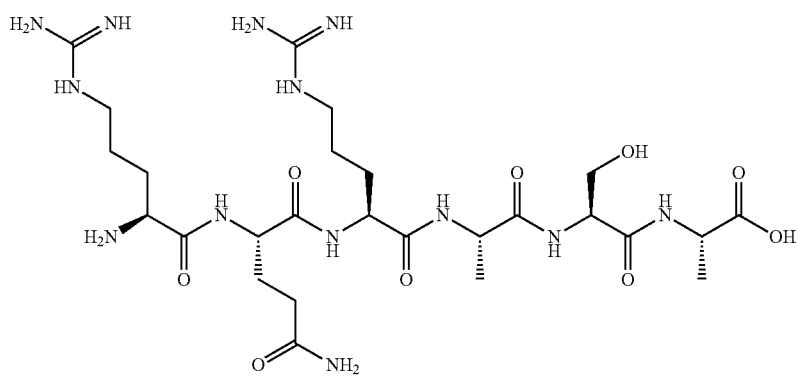

[Formula 3]

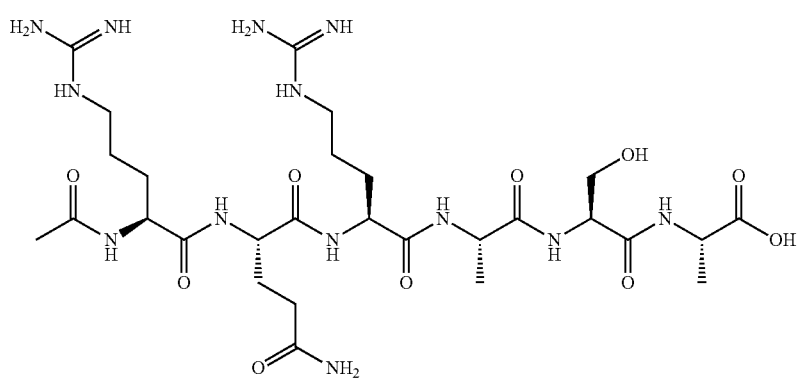

[Formula 4]
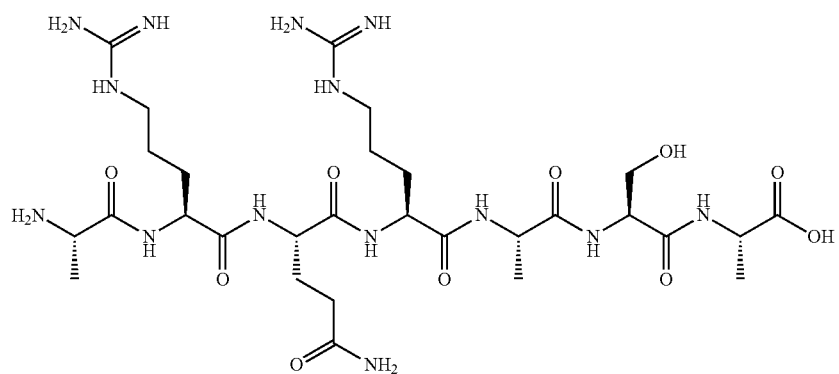
[Formula 5]
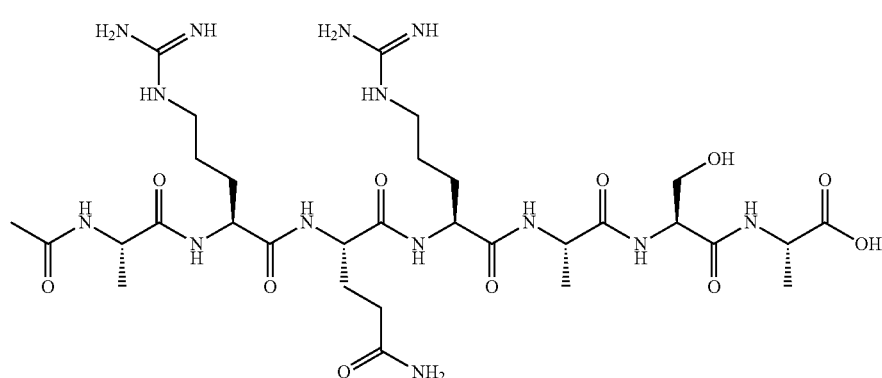
[Formula 6]
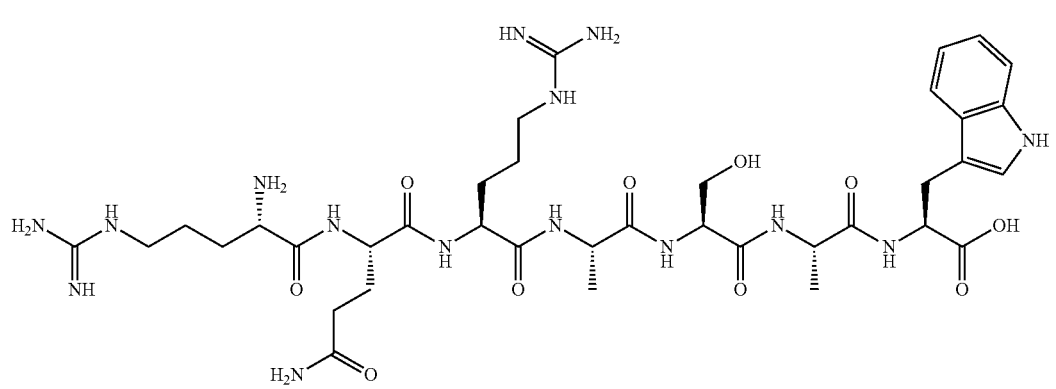
[Formula 7]
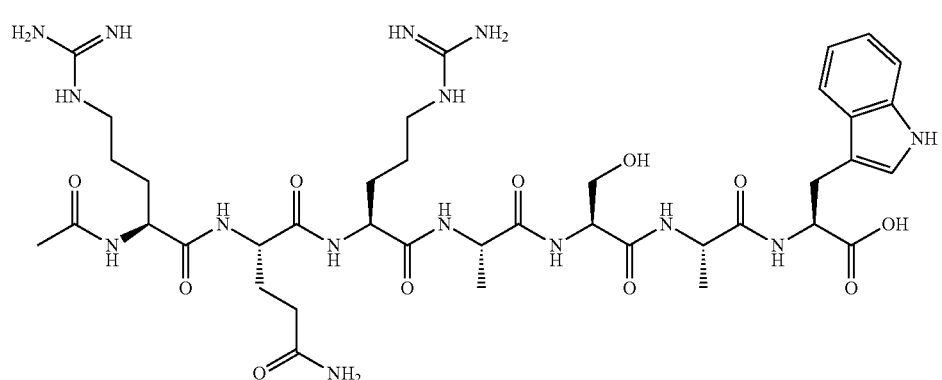

-continued

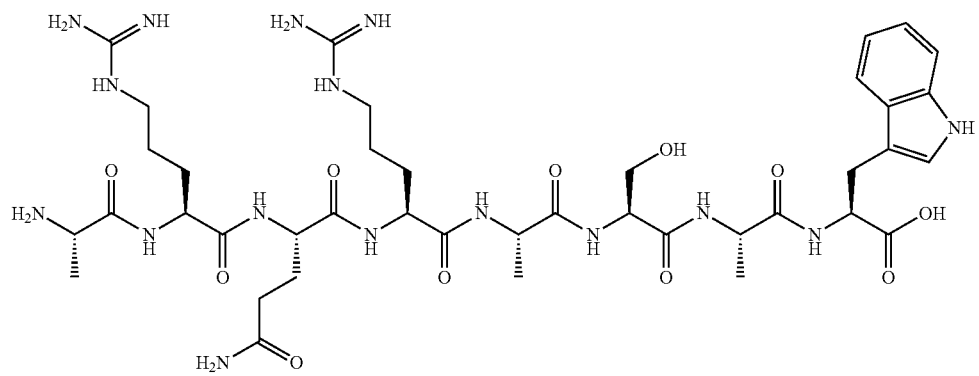

[Formula 8]

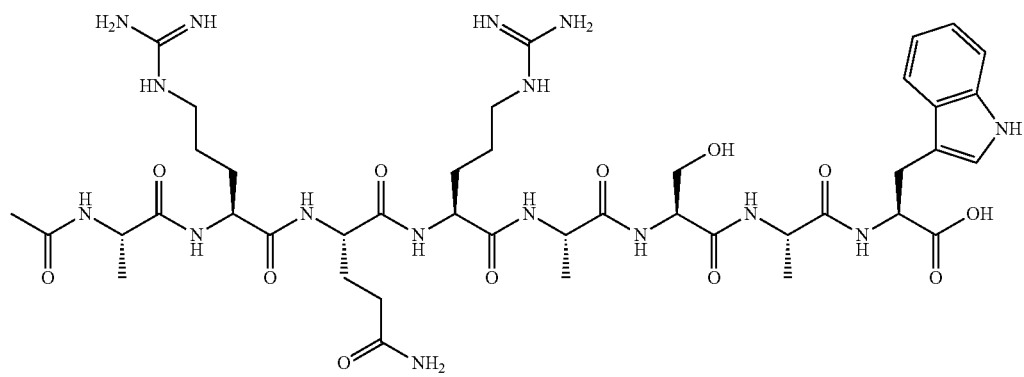

[Formula 9]

The present invention also provides pharmaceutical compositions for preventing and treating allergic and asthmatic diseases including at least one of the peptide derivatives represented by Formula 1 or a salt thereof as an active ingredient.

As used herein, the term "including as an active ingredient" means the presence of the corresponding ingredient in an amount necessary or sufficient to achieve a desired biological effect. In real applications, the active ingredient is used in a therapeutically effective amount to treat a target disease and such an amount can suitably be determined taking into consideration other toxicities caused by the active ingredient. For example, the amount of the active ingredient may vary depending on various factors, such as the disease or condition to be treated, the dosage form of each composition, the size of a subject or the severity of the disease or condition. The effective amount of each composition can be empirically determined by those skilled in the art without excessive experiments.

As described previously, the peptide derivatives of Formula 1 may include the peptide derivatives represented by Formulae 2 to 9.

The pharmaceutical compositions of the present invention can be used to prevent and treat a wide range of allergic and asthmatic diseases. Examples of the allergic diseases include, but are not limited to, atopic dermatitis, rash, and allergic rhinitis.

The compositions of the present invention may be complexed with other drugs for the prevention and treatment of allergic and asthmatic diseases before administration or may further include one or more ingredients selected from excipients, diluents, adjuvants, and stabilizers.

The dosage forms of the compositions according to the present invention may vary depending on the mode of administration. Examples of such dosage forms include, but are not limited to, solid, semi-solid, and liquid formulations, such as tablets, pills, powders, capsules, gels, ointments, emulsions, and suspensions. The compositions of the present invention may be administered in unit dosage forms suitable for single administration of precise doses. Depending on desired formulations, the compositions may further include one or more pharmaceutically acceptable excipients, diluents, adjuvants, and stabilizers, which are generally used in the preparation of formulations for human administration. The excipients refer to ingredients defined as aqueous carriers. As the diluents, there may be mentioned, for example, distilled water, physiological saline, Ringer's solution, glucose solution, and Hank's solution. The pharmaceutical compositions of the present invention may also be administered in the form of complexes with one or more other drug preparations or pharmaceutical preparations for the prevention and treatment of allergic and asthmatic diseases. Various kinds of prophylactic and therapeutic drugs for allergic and asthmatic diseases can be taken into consideration by those skilled in the art. Such additional ingredients as excipients, diluents, adjuvants, and stabilizers may be used in amounts effective to acquire pharmaceutically acceptable formulations in view of the solubility, biological activity, and other characteristics of the active ingredient.

The stabilizers may be selected from the group consisting of proteins, carbohydrates, buffers, and mixtures thereof.

MODE FOR CARRYING OUT THE INVENTION

The present invention will be explained in more detail with reference to the following examples. These examples are provided to assist in understanding the invention and are not intended to limit the scope of the invention.

Example 1: Synthesis of the Inventive Peptide Derivatives

The peptide derivatives of Formulae 2 to 9 were synthesized by the following procedure.

Figure 1B:
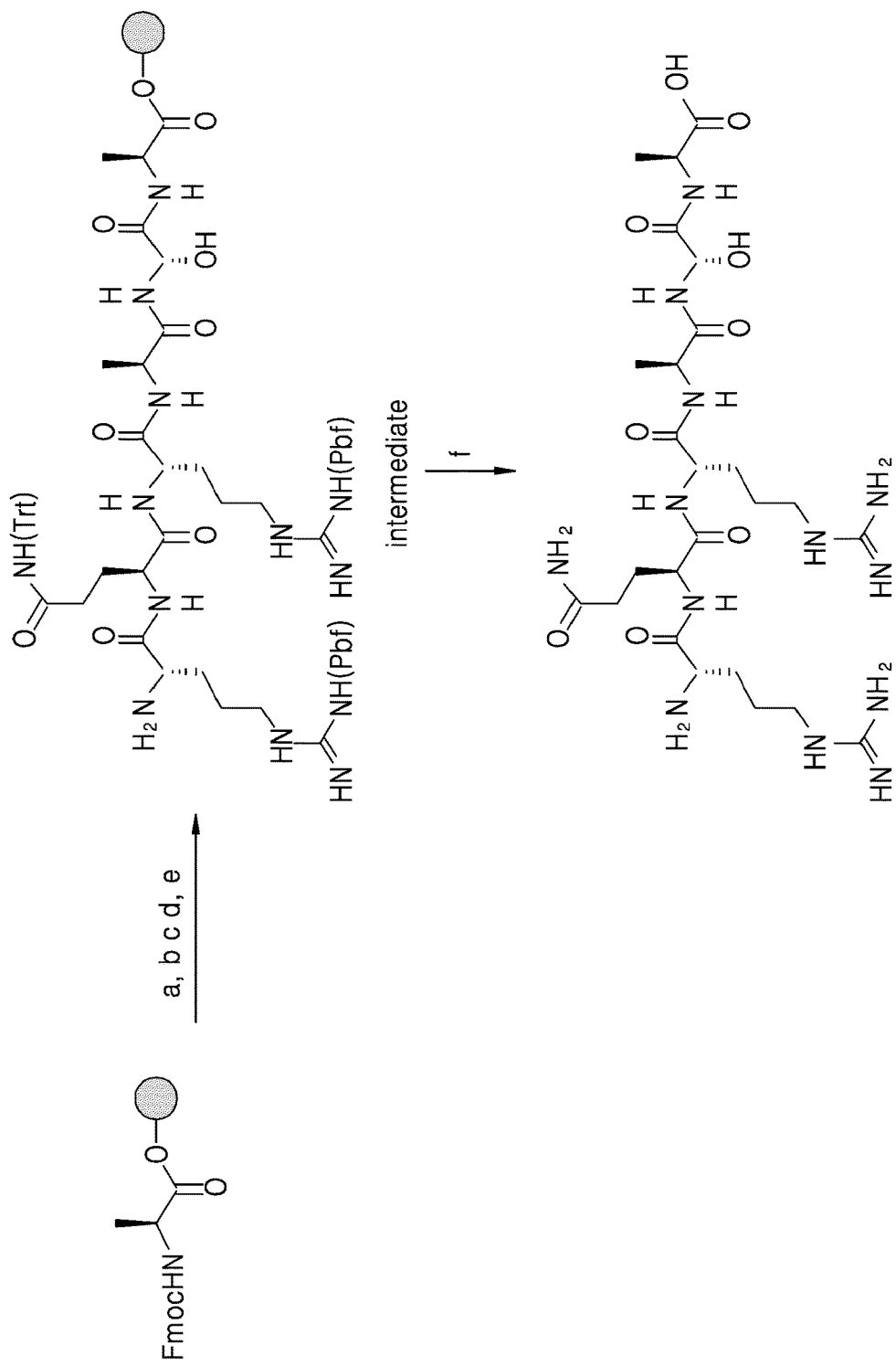
Figure 1C:
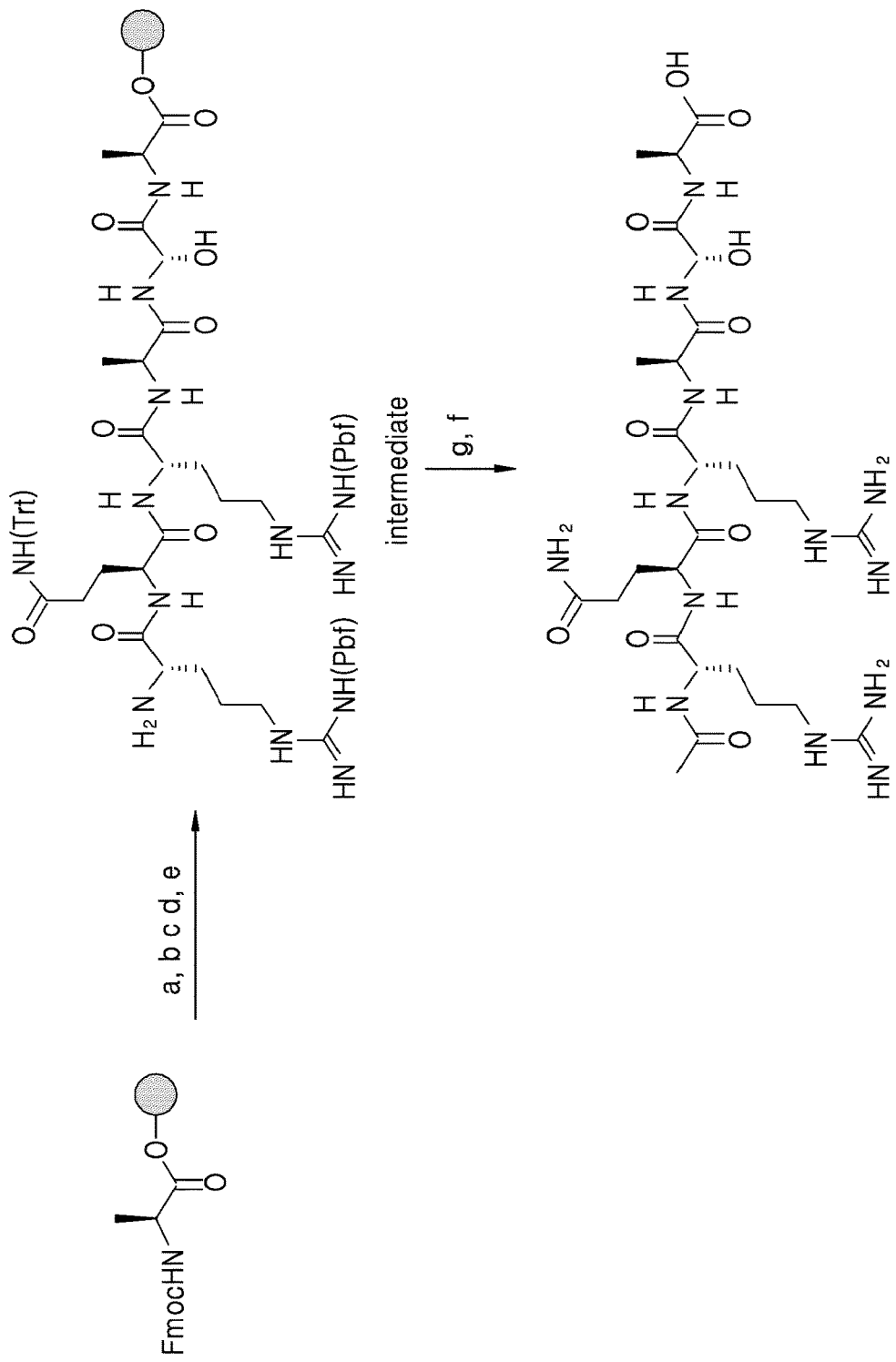
Figure 1D:
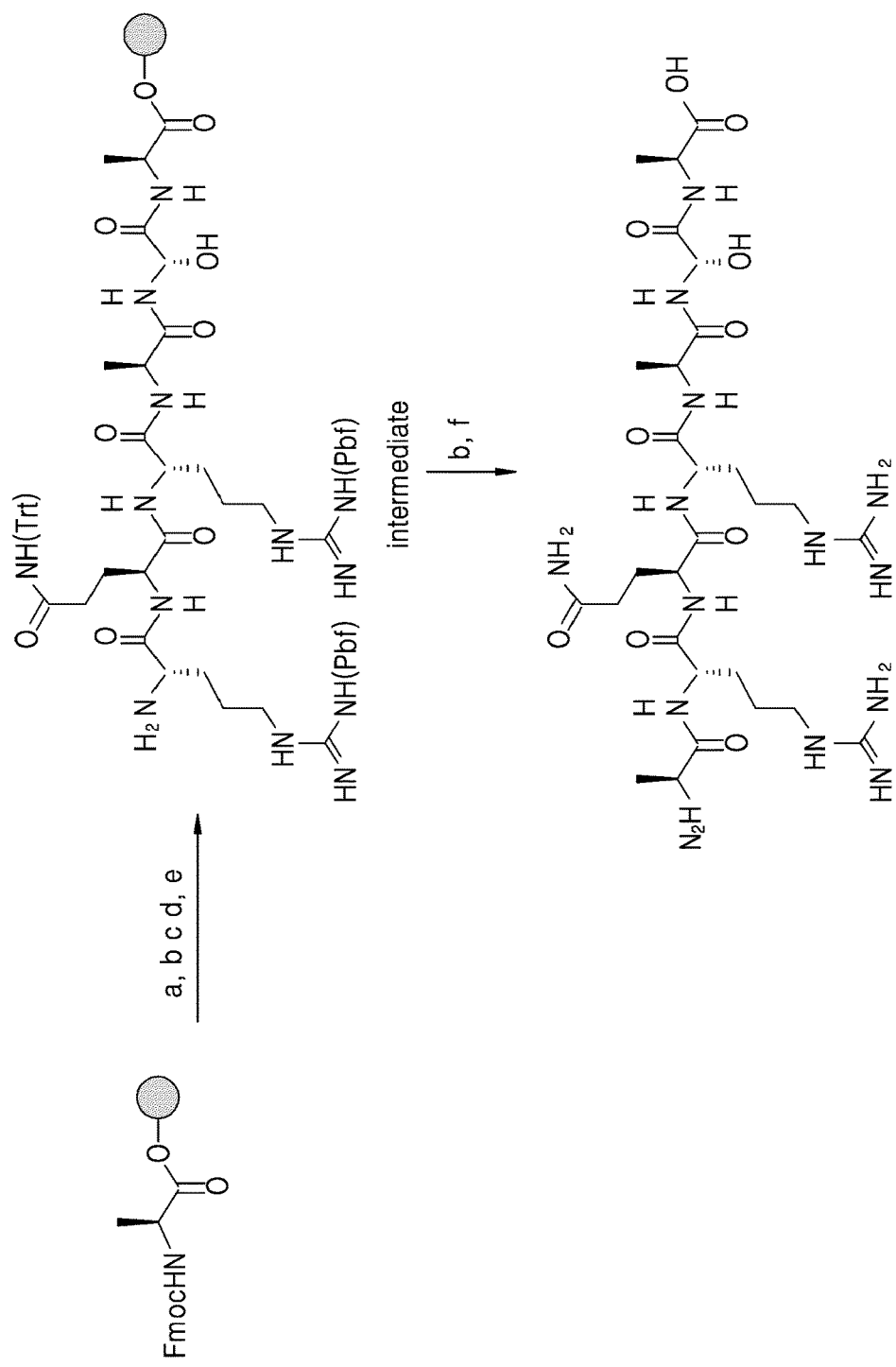
Figure 1E:
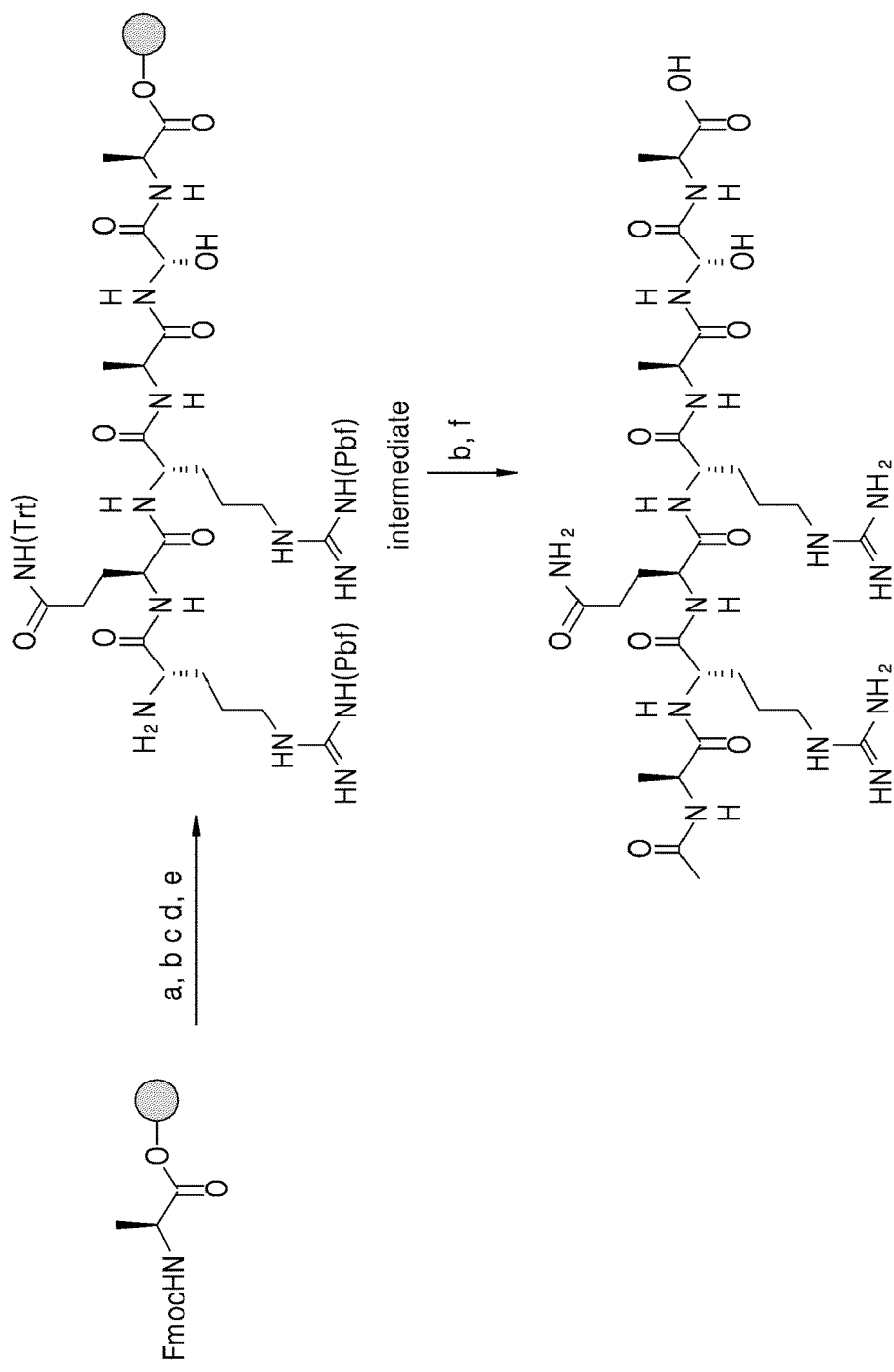

Amino acid sequences were synthesized by the solid phase method using 9-fluorenylmethoxycarbonyl (Fmoc) as a protecting group for the N-amino groups of amino acids. A schematic overview of the synthesis of the peptide derivatives represented by Formulae 2 to 5 is shown in FIGS. 1a to 1e. Reactants used in the reactions shown in FIGS. 1a to 1e and the reaction conditions are as follows:

(a) (i) Piperidine 20%/DMF, 40 min; (ii) Fmoc-Ser-OH, HBTU, DIPEA, HOBt, DMF, 2 h;

(b) (i) Piperidine 20%/DMF, 40 min, room temperature; (ii) Fmoc-Ala-OH, HBTU, DIPEA, HOBt, DMF, 2 h;

(c) (i) Piperidine 20%/DMF, 40 min; (ii) Fmoc-Arg(pbf)-OH, HBTU, DIPEA, HOBt, DMF, 3 h;

(d) (i) Piperidine 20%/DMF, 40 min, room temperature; (ii) Fmoc-Gln(trt)-OH, HBTU, DIPEA, HOBt, DMF, 3 h;

(e) (i) Piperidine 20%/DMF, 40 min; (ii) Fmoc-Arg(pbf)-OH, HBTU, DIPEA, HOBt, DMF, 3 h;

(f) TFA/thioanisole/$H_2O$ (95:2.5:2.5), 3 h; and (g) $Ac_2O$, DIPEA, DMF, 1 h.

Specifically, Fmoc-Ala-Wang-resin was used as a starting material and the extension of peptide chains by coupling of Fmoc-amino acids were performed using N-hydroxybenzotriazole (HOBt) and O-(benzotriazol-1-yl)-N,N,N,N-tetramethyluronium hexafluorophosphate (HBTU). After the Fmoc-amino acid at the amino terminus of each peptide was coupled, the Fmoc group was removed with a 20% piperidine/N-methylpyrrolidone (NMP) solution, washed several times with NMP and dichloromethane (DCM), and dried with nitrogen gas. A trifluoroacetic acid (TFA)-thioanisole-water (95:2.5:2.5 vol./vol.) solution was added, the protecting group was removed, and the peptide was separated from the resin and precipitated with diethyl ether. The resulting crude peptide was purified on a reverse-phase HPLC column by an acetonitrile gradient method using 0.1 TFA-containing acetonitrile and 0.1% TFA-containing water as the eluents.

Figure 1F:
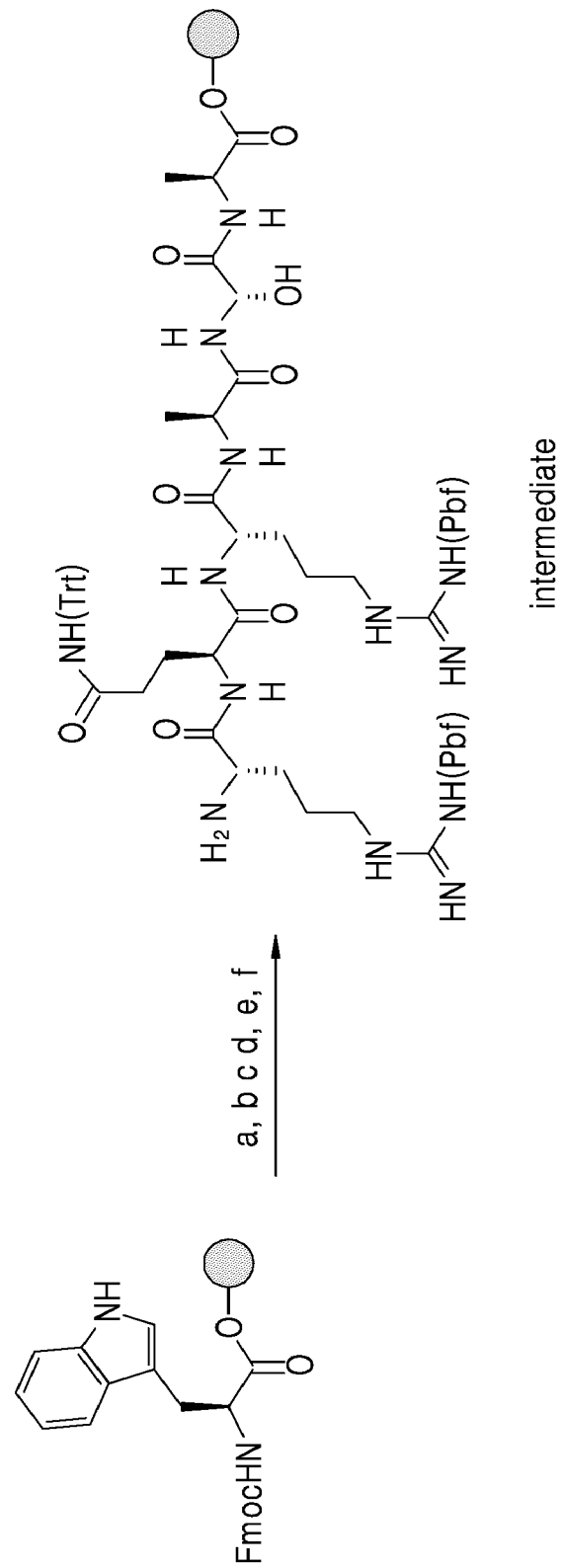
Figure 1G:
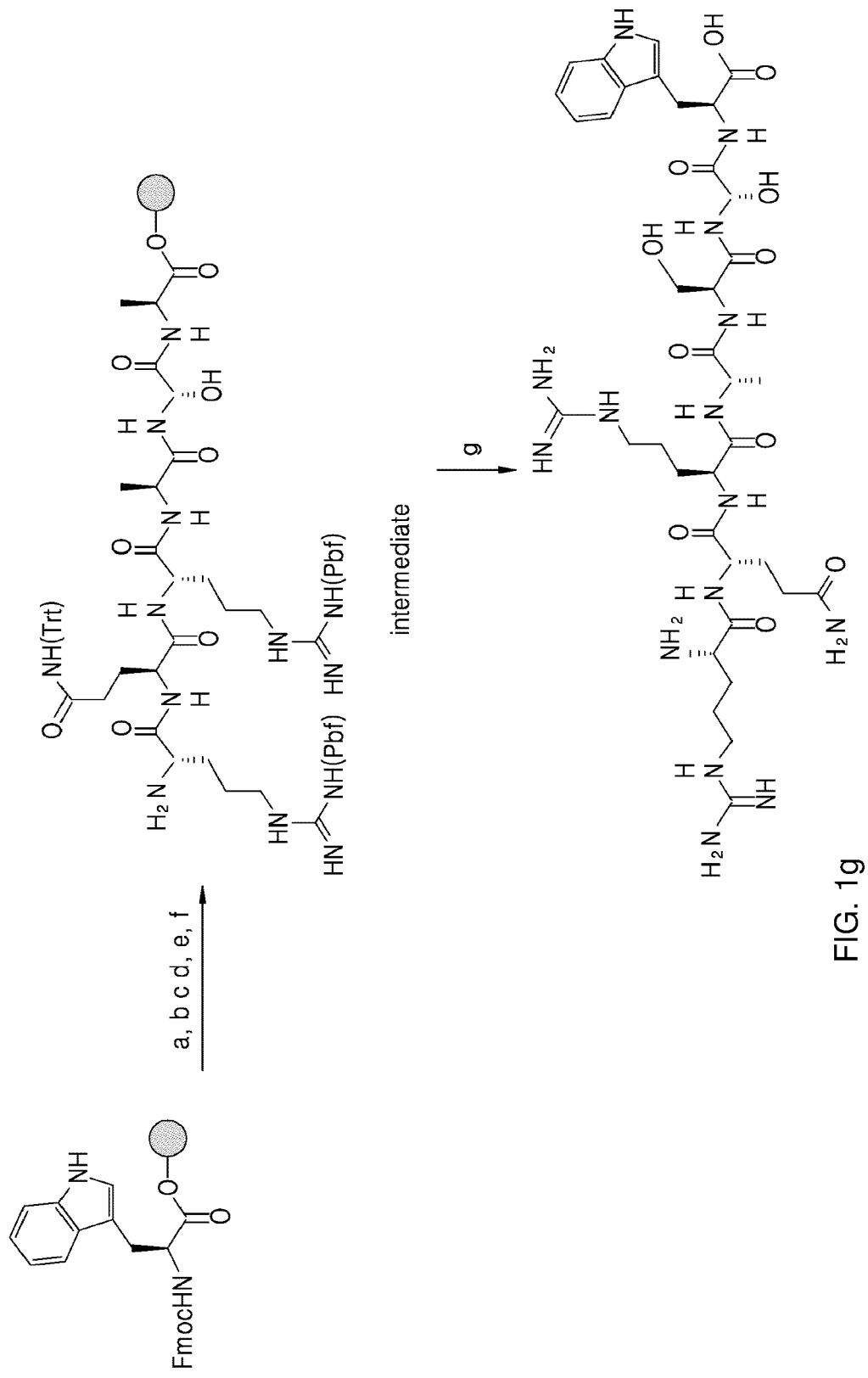
Figure 1H:
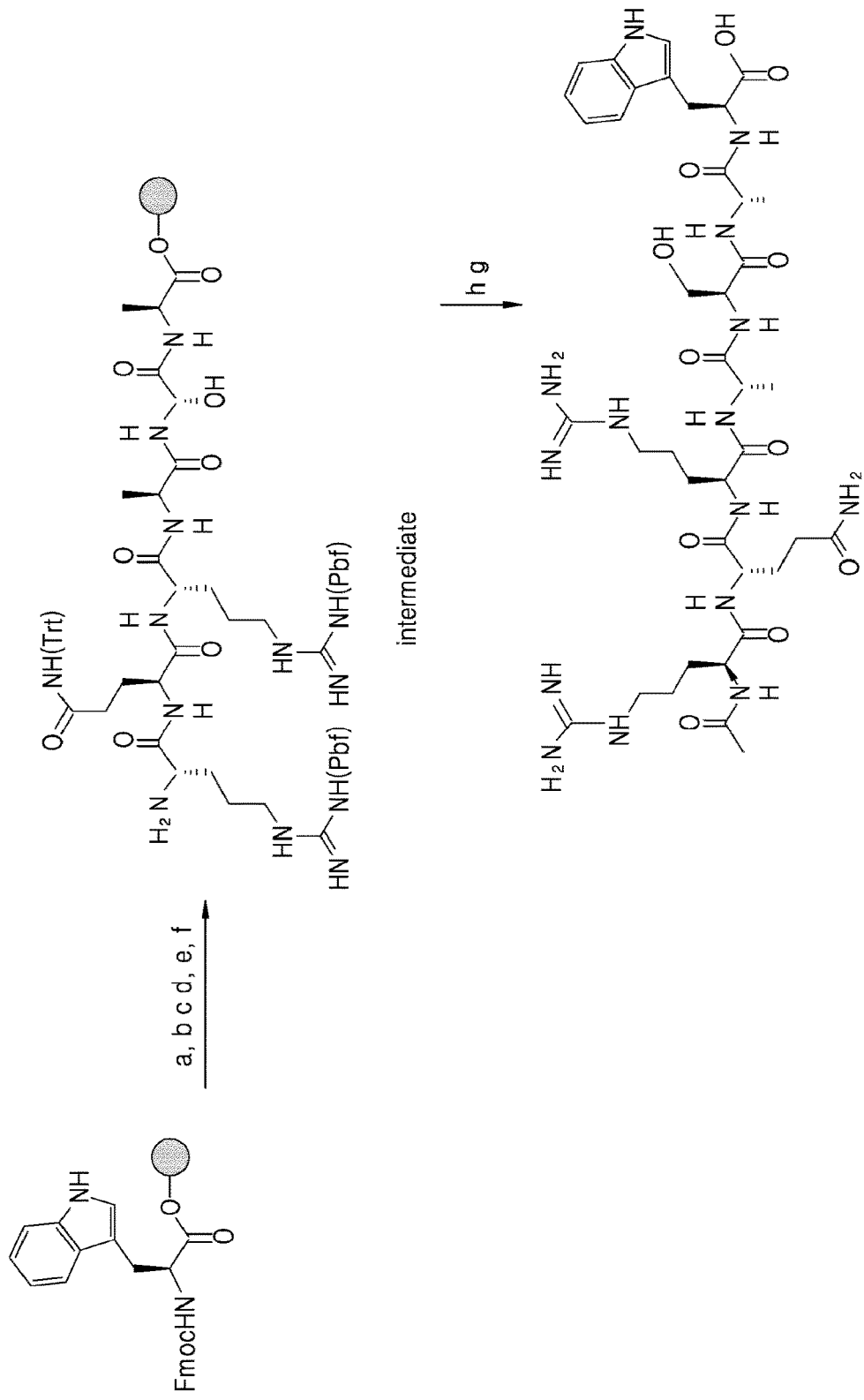
Figure 1J:
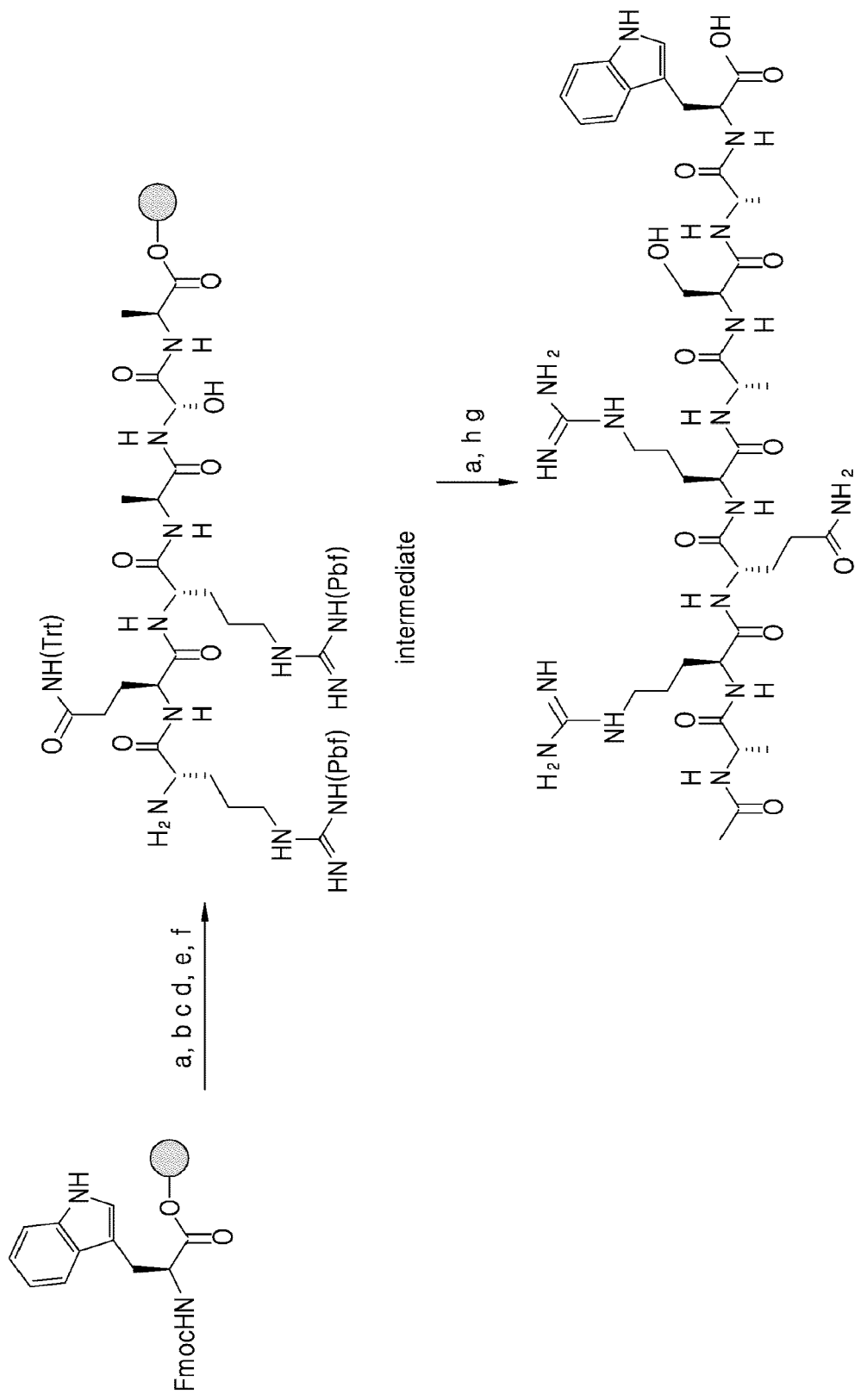

A schematic overview of the synthesis of the peptide derivatives represented by Formulae 6 to 9 is shown in FIGS. 1f to 1j. Reactants used in the reactions shown in FIGS. 1f to 1j and the reaction conditions are as follows:

(a) (i) Piperidine 20%/DMF, 40 min; (ii) Fmoc-Ala-OH, HBTU, DIPEA, HOBt, DMF, 2 h;

(b) (i) Piperidine 20%/DMF, 40 min; (ii) Fmoc-Ser-OH, HBTU, DIPEA, HOBt, DMF, 2 h;

(c) (i) Piperidine 20%/DMF, 40 min, room temperature; (ii) Fmoc-Ala-OH, HBTU, DIPEA, HOBt, DMF, 2 h;

(d) (i) Piperidine 20%/DMF, 40 min; (ii) Fmoc-Arg(pbf)-OH, HBTU, DIPEA, HOBt, DMF, 3 h;

(e) (i) Piperidine 20%/DMF, 40 min; (ii) Fmoc-Gln(trt)-OH, HBTU, DIPEA, HOBt, DMF, 3 h;

(f) (i) Piperidine 20%/DMF, 40 min; (ii) Fmoc-Arg(pbf)-OH, HBTU, DIPEA, HOBt, DMF, 3 h;

(g) TFA/thioanisole/$H_2O$ (95:2.5:2.5), 3 h; and (h) $Ac_2O$, DIPEA, DMF, 1 h.

Below are NMR data for the compounds of Formulae 2 to 9.

Compound 2: Amino Acid Sequence ($H_2$N-Arg-Gln-Arg-Ala-Ser-Ala-COOH) (SEQ ID NO:1)

$^1$H NMR (300 MHz, $D_2O$ and $CD_3CN$): δ 4.28 (m, 5H), 3.94 (t, J=6.3 Hz, 1H), 3.74 (d, J=5.1 Hz, 2H), 3.11 (m, 6H), 2.42 (t, J=7.1 Hz, 1H), 2.30 (t, J=7.1 Hz, 1H), 1.91-1.45 (m, 10H), 1.36 (d, J=7.5 Hz, 3H), 1.34 (d, J=7.9 Hz, 3H); ESI-MS: m/z calcd for $C_{25}H_{47}N_{13}O_9$ [M+H]$^+$ 688.8, found 690.0.

Compound 3: Amino Acid Sequence ($CH_3$CONH-Arg-Gln-Arg-Ala-Ser-Ala-COOH) (SEQ ID NO:2)

$^1$H NMR (300 MHz, $D_2O$): δ 4.31 (t, J=5.4 Hz, 1H), 4.27-4.12 (m, 5H), 3.76 (d, J=5.3 Hz, 2H), 3.10 (t, J=6.6 Hz, 4H), 2.30 (t, J=7.1 Hz, 4H), 1.92 (s, 3H), 2.12-1.71 (m, 3H), 1.70-1.48 (m, 8H), 1.32 (d, J=7.3 Hz, 3H), 1.34 (d, J=7.9 Hz, 3H); ESI-MS: m/z calcd for $C_{27}H_{49}N_{13}O_{10}$ [M+H]$^+$ 730.8, found 730.9.

Compound 4: Amino Acid Sequence ($H_2$N-Ala-Arg-Gln-Arg-Ala-Ser-Ala-COOH) (SEQ ID NO:3)

$^1$H NMR (300 MHz, $D_2O$): δ 4.45-4.18 (m, 6H), 4.35 (m, 6H), 3.83 (d, J=5.3 Hz, 2H), 3.17 (t, J=6.5 Hz, 4H), 3.30-3.11 (m, 1H), 2.35 (t, J=7.4 Hz, 2H), 2.17-1.94 (m, 2H), 1.92-1.54 (m, 12H), 1.48 (d, J=7.1 Hz, 4H), 1.37 (t, J=6.7 Hz, 8H); ESI-MS: m/z calcd for $C_{28}H_{52}N_{14}O_{10}$ [M+H]$^+$ 759.8, found 759.3.

Compound 5: Amino Acid Sequence ($CH_3$CONH-Ala-Arg-Gln-Arg-Ala-Ser-Ala-COOH) (SEQ ID NO:4)

$^1$H NMR (300 MHz, $D_2O$): δ 4.31 (t, J=5.6 Hz, 1H), 4.26-4.11 (m, 5H), 3.76 (d, J=5.2 Hz, 2H), 3.55 (t, J=7.1 Hz, 4H), 3.09 (t, J=6.8 Hz, 2H), 1.92 (s, 3H), 2.05-1.45 (m, 11H), 1.31 (d, J=7.3 Hz, 3H), 1.30 (d, J=7.2 Hz, 3H), 1.24 (d, J=7.2 Hz, 3H); ESI-MS: m/z calcd for $C_{30}H_{54}N_{14}O_{11}$ [M+H]$^+$ 801.9, found 801.6.

Compound 6: Amino Acid Sequence ($H_2$N-Arg-Gln-Arg-Ala-Ser-Ala-Trp-COOH) (SEQ ID NO:5)

$^1$H NMR (300 MHz, $D_2O$): δ 7.65 (d, J=7.8 Hz, 1H), 7.48 (d, J=8.1 Hz, 1H), 7.26-7.10 (m, 3H), 4.42-4.19 (m, 5H), 4.03 (t, J=6.5 Hz, 1H), 3.80-3.66 (m, 2H), 3.42-2.98 (m, 6H), 2.37 (t, J=7.5 Hz, 2H), 2.14-1.53 (m, 11H), 1.37 (d, J=7.2 Hz, 3H), 1.25 (d, J=7.2 Hz, 3H); LRMS ESI m/z calcd for $C_{37}H_{59}N_{15}O_{10}$ [M+H]$^+$ 874.0, found 875.0.

Compound 7: Amino Acid Sequence ($CH_3$CONH-Arg-Gln-Arg-Ala-Ser-Ala-Trp-COOH) (SEQ ID NO:6)

$^1$H NMR (300 MHz, $D_2O$): δ 7.57 (d, J=7.8 Hz, 1H), 7.41 (d, J=8.1 Hz, 1H), 7.20-7.03 (m, 3H), 4.30-4.11 (m, 5H), 3.74-3.59 (m, 2H), 3.35-3.00 (m, 6H), 2.28 (t, J=7.4 Hz, 2H), 2.08-1.45 (m, 14H), 1.30 (d, J=7.2 Hz, 3H), 1.18 (d, J=7.2 Hz, 3H); LRMS ESI m/z calcd for $C_{39}H_{61}N_{15}O_{11}$ [M+H]$^+$ 916.0, found 916.8.

Compound 8: Amino Acid Sequence ($H_2$N-Ala-Arg-Gln-Arg-Ala-Ser-Ala-Trp-COOH) (SEQ ID NO:7)

$^1$H NMR (300 MHz, $D_2O$): δ 7.55 (d, J=7.2 Hz, 1H), 7.39 (d, J=8.1 Hz, 1H), 7.20-7.01 (m, 3H), 4.32-4.11 (m, 7H), 4.05-3.94 (m, 1H), 3.73-3.58 (m, 2H), 3.34-3.00 (m, 6H), 2.27 (t, J=7.7 Hz, 2H), 2.05-1.47 (m, 11H), 1.41 (d, J=7.2 Hz, 3H), 1.27 (d, J=7.2 Hz, 3H), 1.15 (d, J=7.2 Hz, 3H); LRMS ESI m/z calcd for $C_{40}H_{64}N_{16}O_{11}$ [M+H]$^+$ 945.0, found 945.8.

Compound 9: Amino Acid Sequence ($CH_3$CONH-Ala-Arg-Gln-Arg-Ala-Ser-Ala-Trp-COOH) (SEQ ID NO:8)

$^1$H NMR (300 MHz, $D_2O$): δ 7.62 (d, J=7.5 Hz, 1H), 7.45 (d, J=8.1 Hz, 1H), 7.25-7.07 (m, 3H), 4.35-4.14 (m, 7H), 3.79-3.63 (m, 2H), 3.40-3.06 (m, 6H), 2.32 (t, J=7.2 Hz, 2H), 2.11-1.50 (m, 14H), 1.34 (d, J=7.5 Hz, 3H), 1.32 (d, J=8.4 Hz, 3H), 1.22 (d, J=6.9 Hz, 3H); LRMS ESI m/z calcd for $C_{42}H_{66}N_{16}O_{12}$ [M+H]$^+$ 987.1, found 988.2.

Example 2: Cell-Based Efficacy Evaluation Using FACS

The binding of TSLP to its receptor activates various signaling pathways, mainly the JAK/STAT pathway. TSLP signaling is also known to specifically phosphorylate STAT5 among STAT molecules. In order to confirm whether the inventive compounds effectively inhibit the binding of TSLP to its receptor, it is necessary to determine the degree of phosphorylation of STAT5 molecules in the JAK/STAT pathway activated by this binding. When the inventive compounds effectively inhibit the binding of TSLP to its receptor, the level of phosphorylation of STAT5 molecules can be inhibited.

Figure 2:
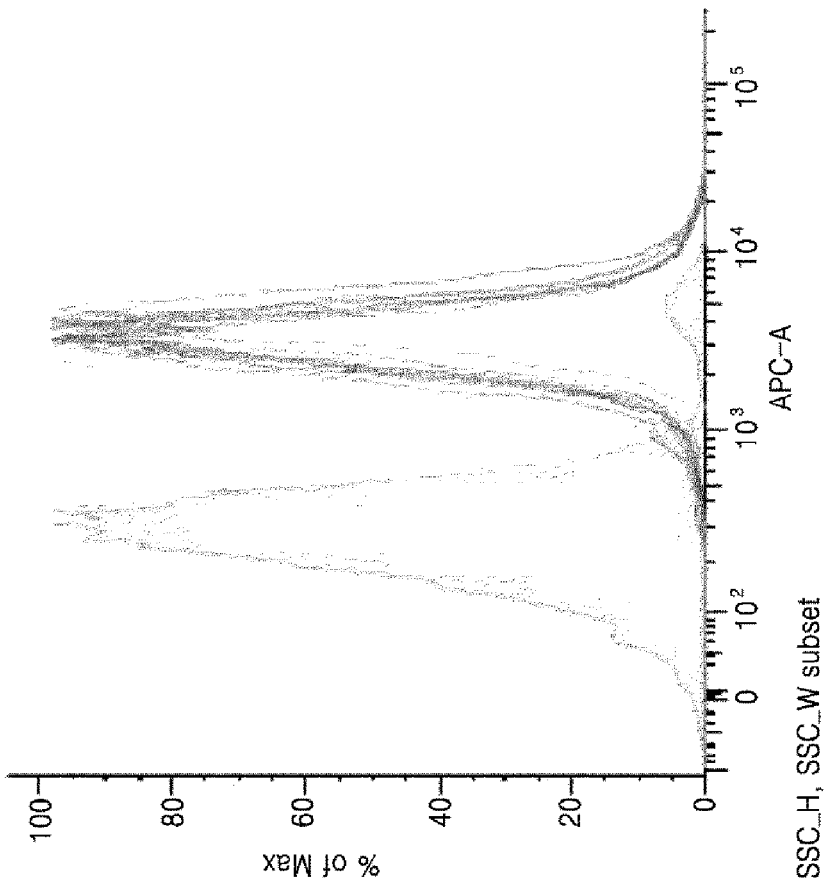
FIG. 2 is a graph showing changes in the intracellular phosphorylation of STAT5 molecules by treatment with the compound of Formula 2 as a TSLP-binding peptide derivative of the present invention.
Figure 3:
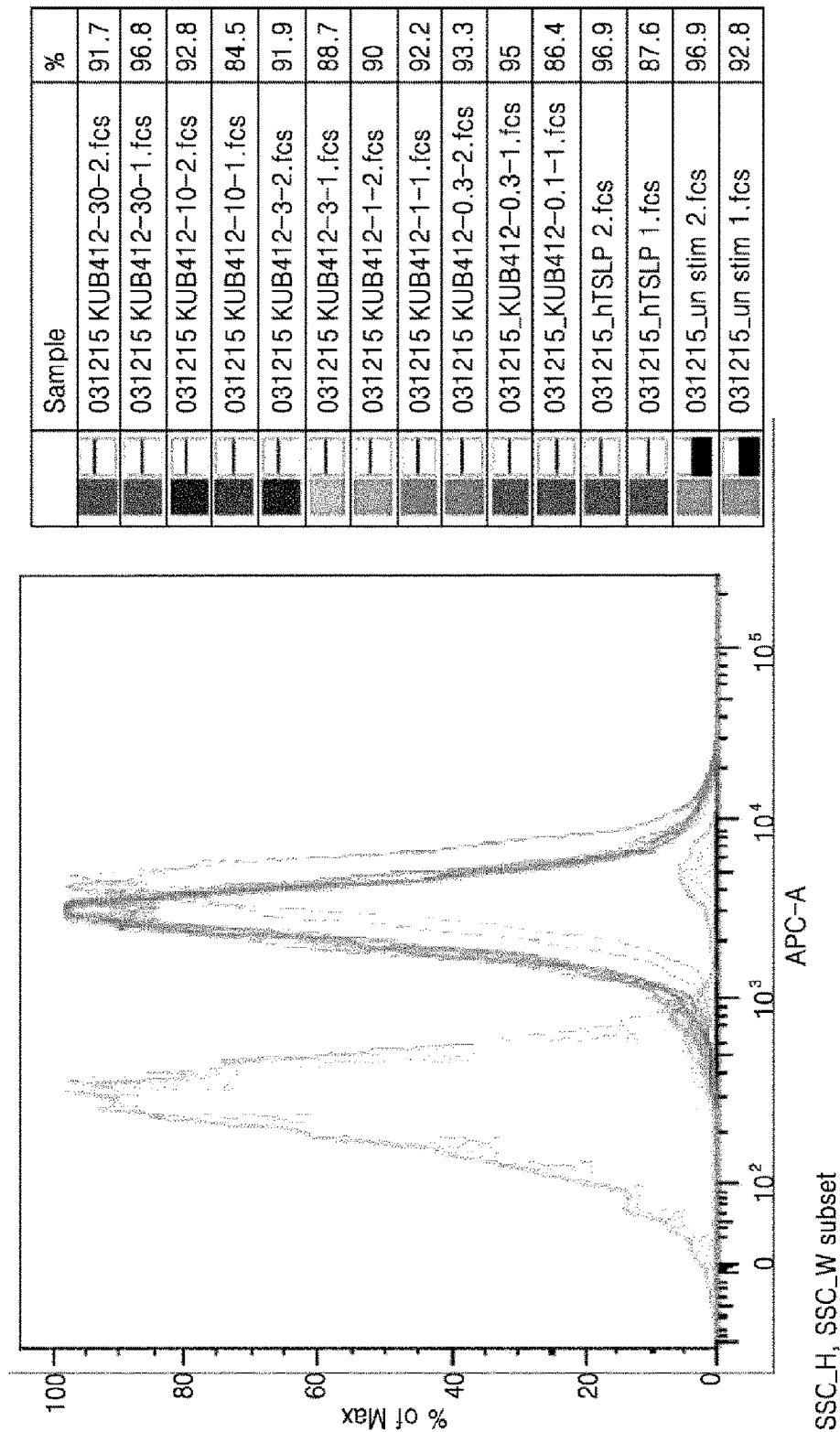
FIG. 3 is a graph showing changes in the intracellular phosphorylation of STAT5 molecules by treatment with the compound of Formula 3 as a TSLP-binding peptide derivative of the present invention.
Figure 4:
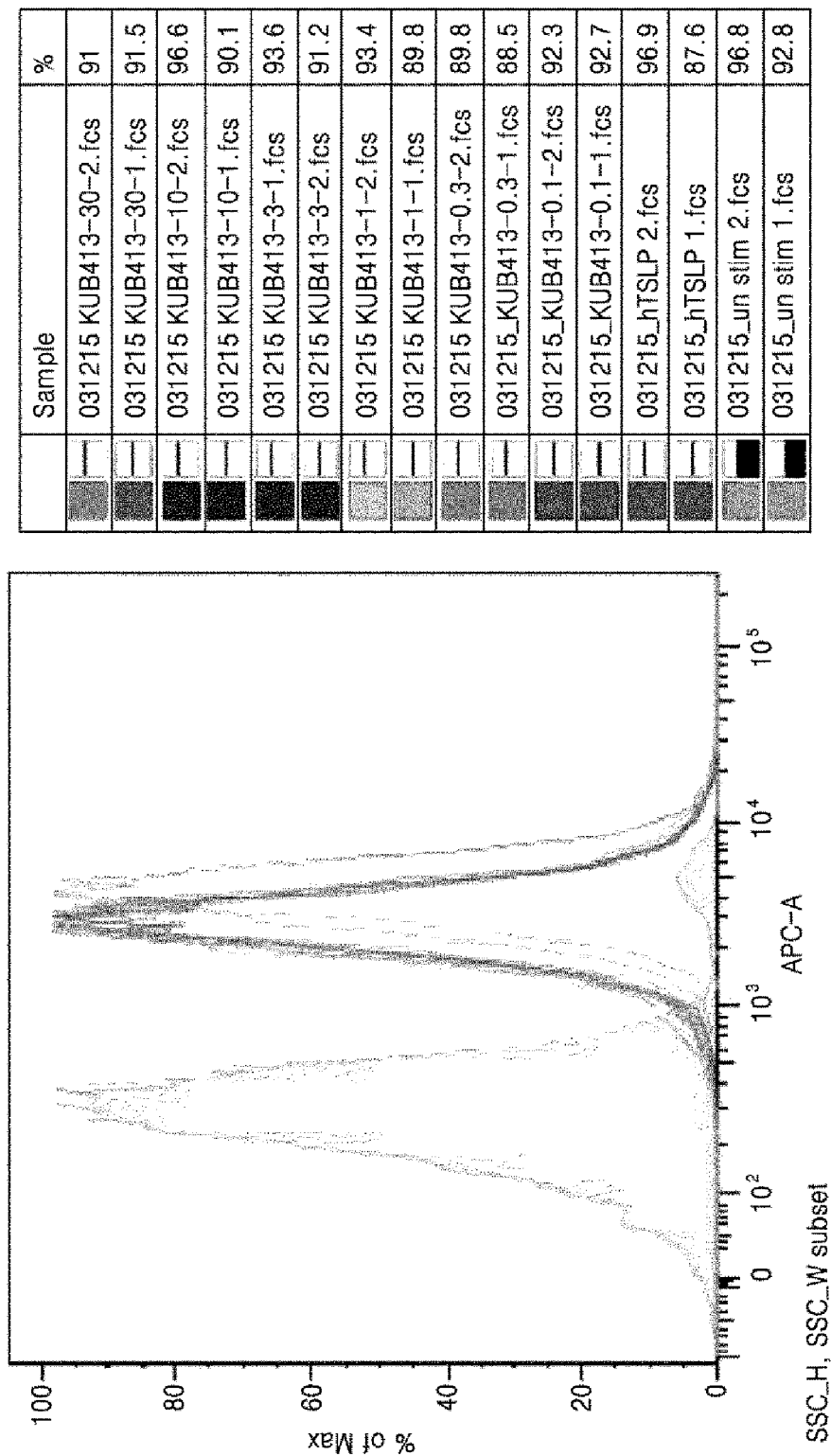
FIG. 4 is a graph showing changes in the intracellular phosphorylation of STAT5 molecules by treatment with the compound of Formula 4 as a TSLP-binding peptide derivative of the present invention.
Figure 5:
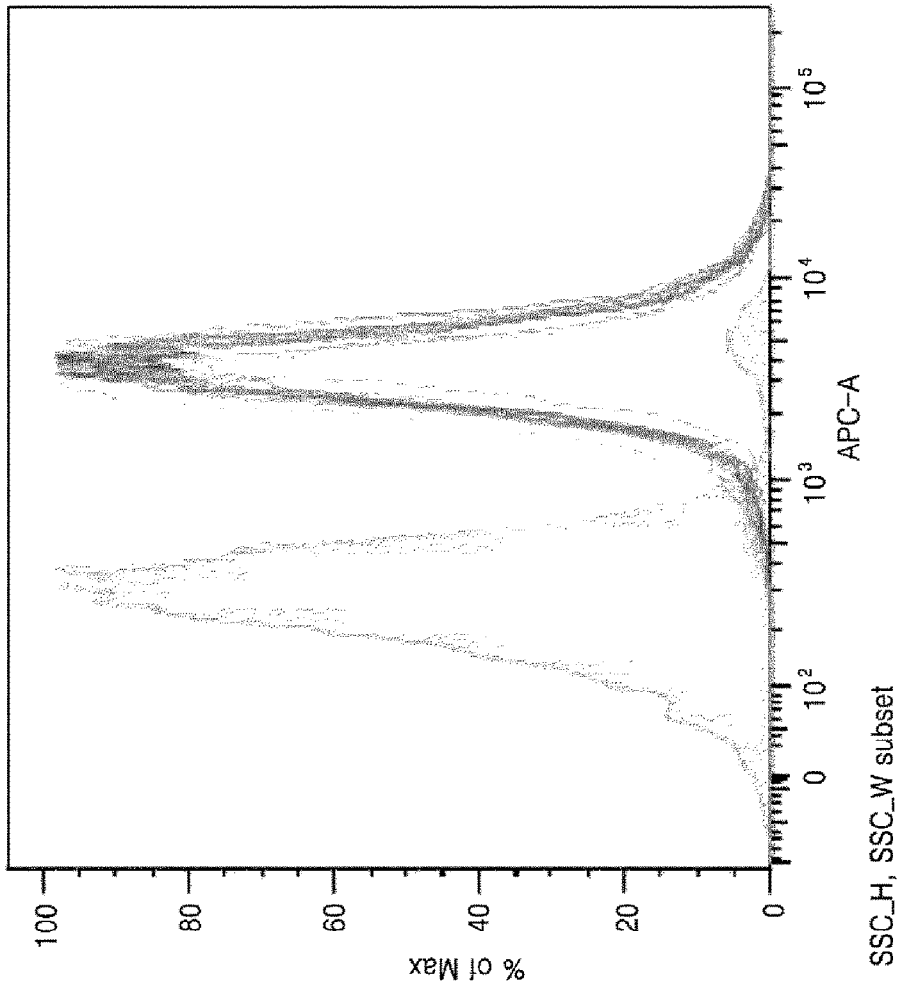
FIG. 5 is a graph showing changes in the intracellular phosphorylation of STAT5 molecules by treatment with the compound of Formula 5 as a TSLP-binding peptide derivative of the present invention.
Figure 6:
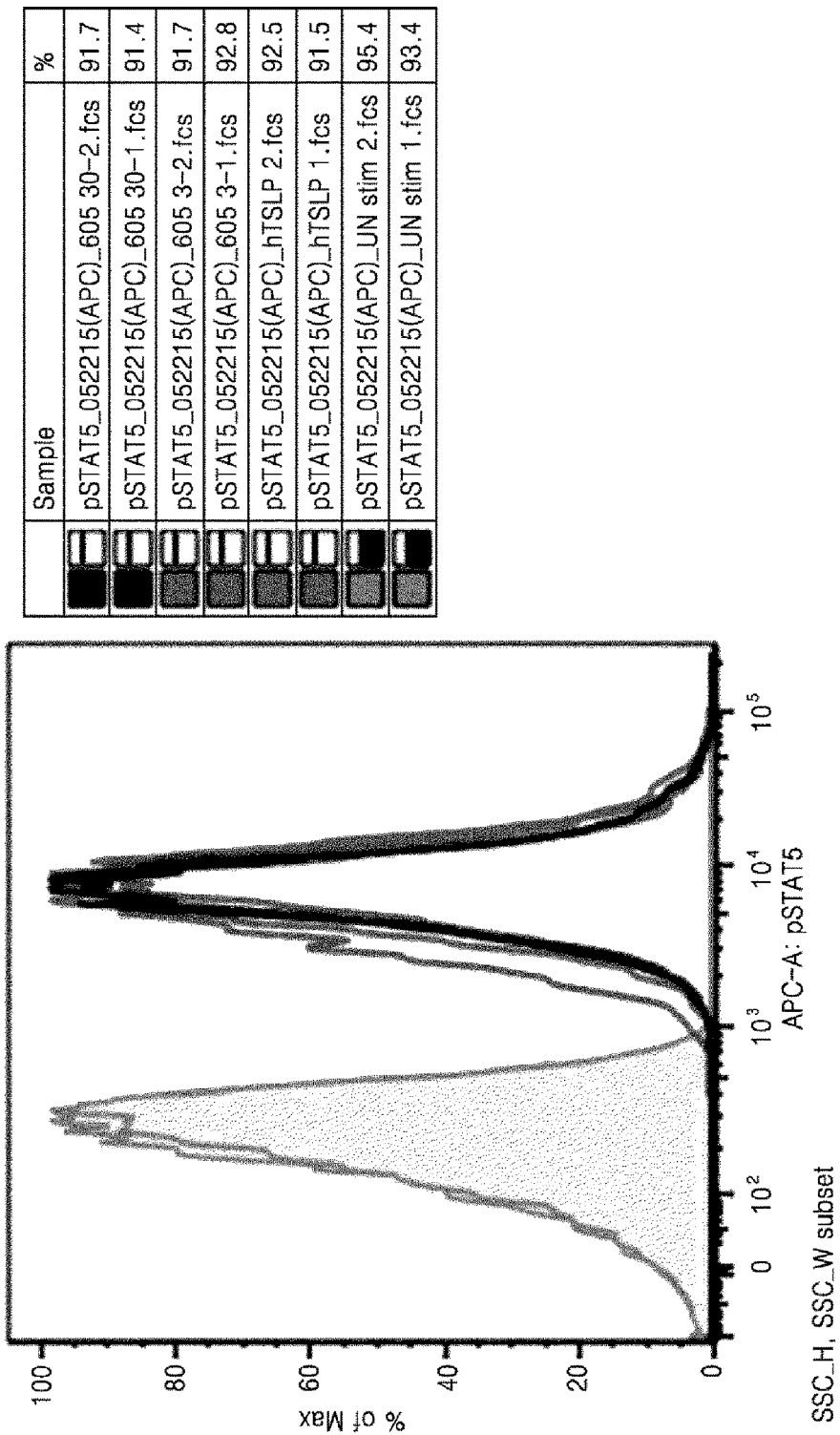
FIG. 6 is a graph showing changes in the intracellular phosphorylation of STAT5 molecules by treatment with the compound of Formula 6 as a TSLP-binding peptide derivative of the present invention.
Figure 7:
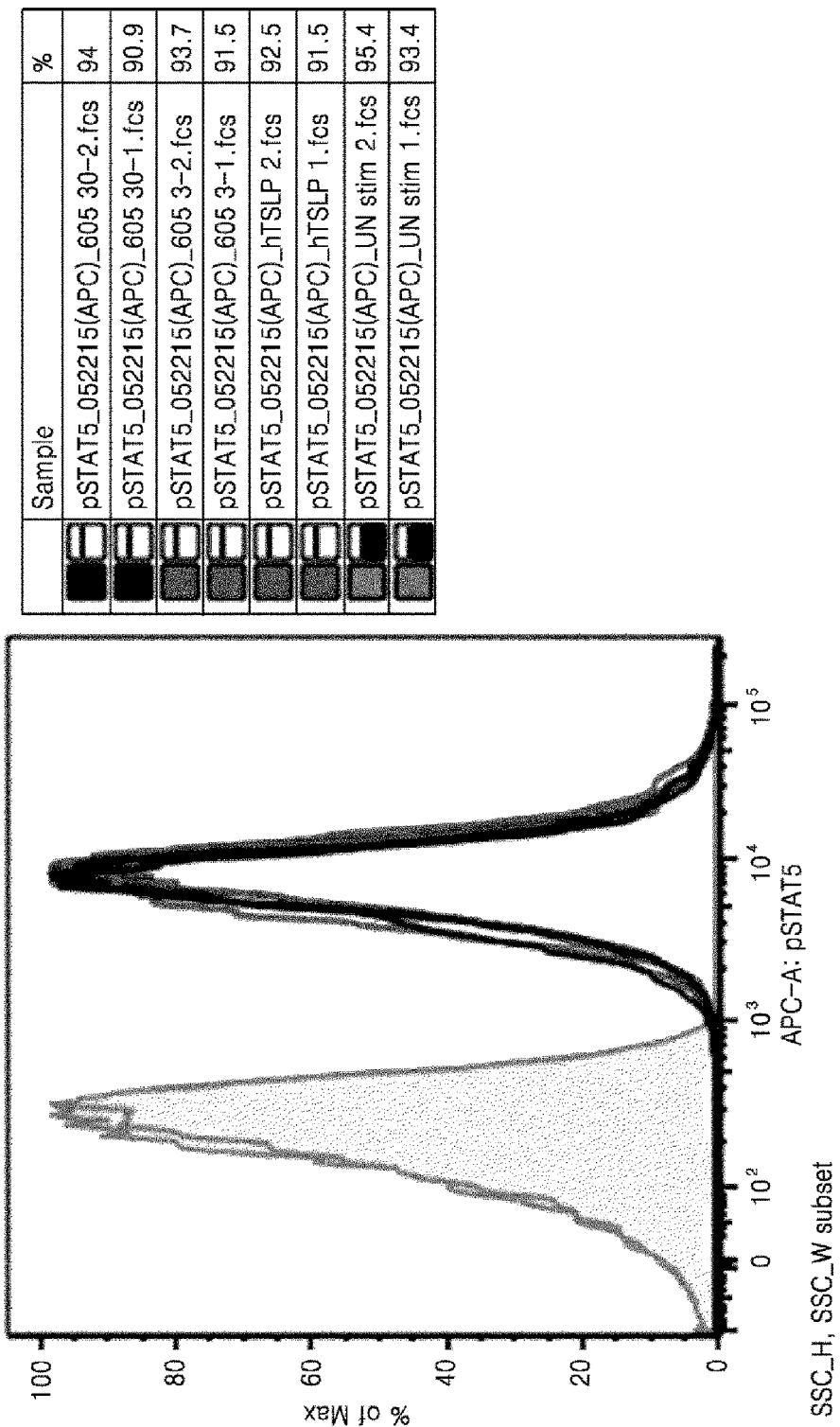
FIG. 7 is a graph showing changes in the intracellular phosphorylation of STAT5 molecules by treatment with the compound of Formula 7 as a TSLP-binding peptide derivative of the present invention.
Figure 8:
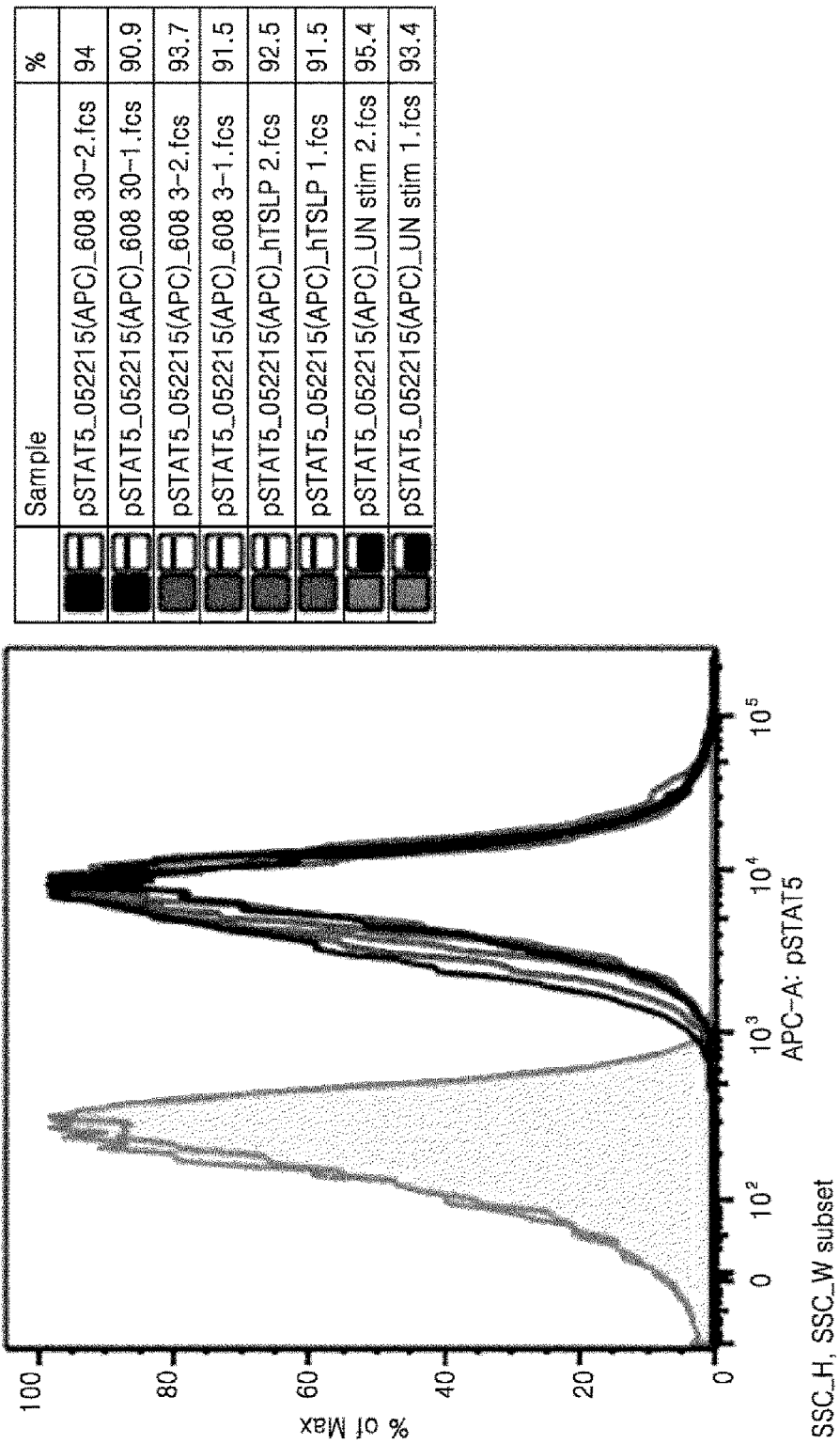
FIG. 8 is a graph showing changes in the intracellular phosphorylation of STAT5 molecules by treatment with the compound of Formula 9 as a TSLP-binding peptide derivative of the present invention.

In this example, this fact was confirmed through the following experiment. First, HMC-1, a human mast cell line, was cultured until an appropriate number of cells were maintained in a 96-well plate. After the supernatant was discarded, mixtures of TSLP (100 ng/mL) and appropriate concentrations (0.3, 3, and 30 µM) of each peptide were treated on cells for 30 min. Cells were fixed with Cytofix. Subsequently, cells were permeabilized with a permeabilization buffer and stained with anti-pSTAT5 antibody at 4° C. for 30 min. Cells were washed three times with the same buffer and analyzed by flow cytometry. FIGS. 2 to 8 show changes in the intracellular phosphorylation of STAT5 molecules by treatment with the compounds of Formulae 2 to 7 and 9, respectively. After the compounds of Formulae 2 to 5 were added at concentrations of 0.3, 3, and 30 µM, the degrees of intracellular phosphorylation of STAT5 molecule were measured and compared with those in a control treated with TSLP alone. The results are shown in Table 1. The intracellular phosphorylation of STAT5 molecules in the control was 100%.

TABLE 1

| Compound | Degrees of phosphorylation of STAT5 molecules in cells (%) | | |
|---|---|---|---|
| | 0.3 µM | 3 µM | 30 µM |
| 2 | 84.4 | 77.9 | 69.8 |
| 3 | 73.5 | 67.8 | 66.9 |
| 4 | 71.0 | 68.3 | 70.9 |
| 5 | 86.1 | 84.6 | 77.1 |

INDUSTRIAL APPLICABILITY

Taken together, the peptide derivatives of the present invention can effectively suppress the binding of TSLP, a cytokine playing a crucial role in causing allergic and asthmatic diseases, to its receptor. Therefore, the peptide derivatives of the present invention inhibit TSLP-mediated signal transduction, indicating that the peptide derivatives of the present invention can be used to fundamentally prevent and treat allergic and asthmatic diseases.

What is claimed is:
1. A peptide derivative represented by Formula 1:

[Formula 1]

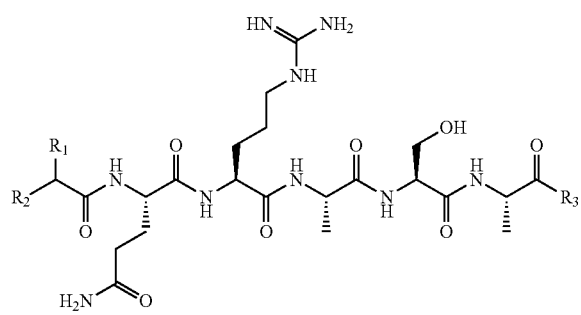

wherein $R_1$ is a guanidine-substituted $C_1$-$C_4$ alkyl group, $R_2$ is selected from an amine groups and the following structures 1:

[Structures 1]

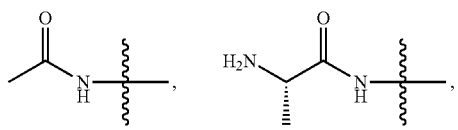

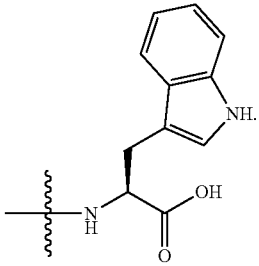

and $R_3$ is selected from a hydroxyl group and the following structure 2:

[Structure 2]

2. The peptide derivative according to claim 1, wherein the peptide derivative of Formula 1 is selected from those represented by Formulae 2 to 9:

[Formula 2]

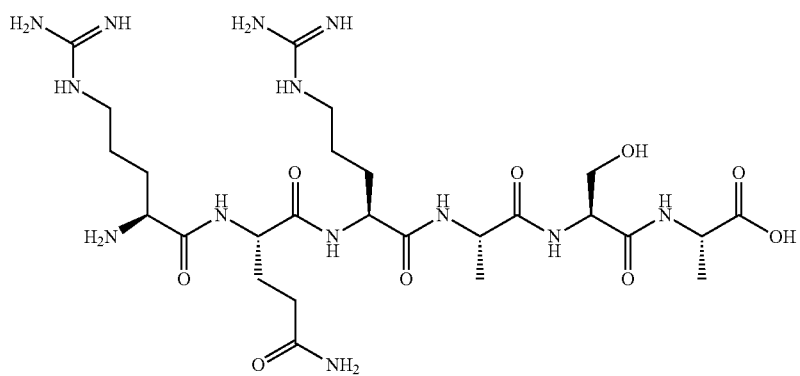

[Formula 3]

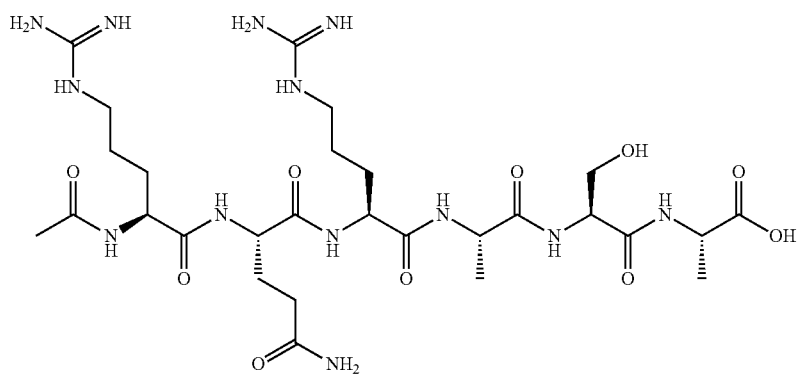

[Formula 4]
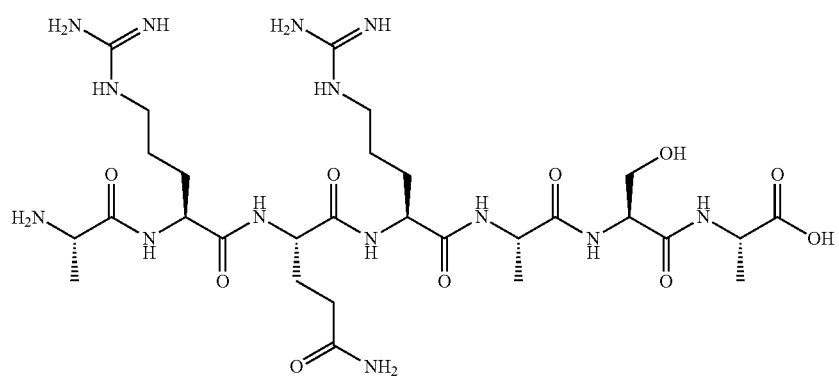
[Formula 5]
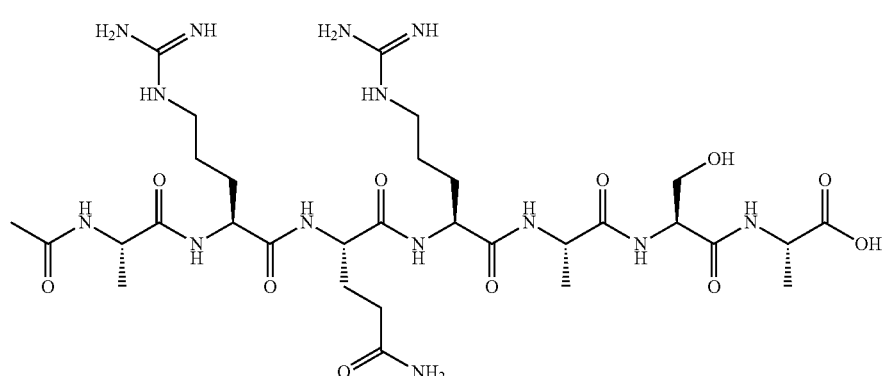
[Formula 6]
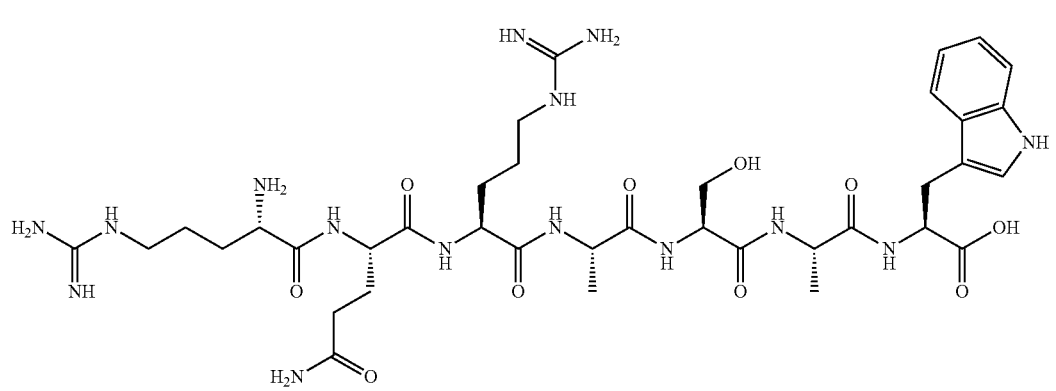
[Formula 7]
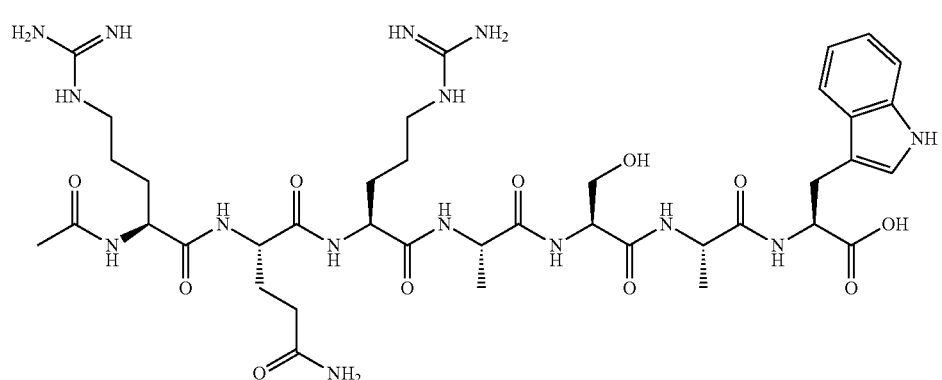

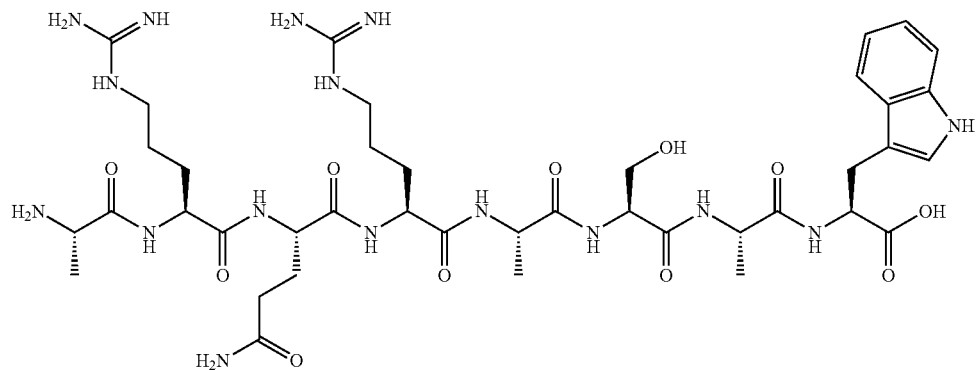

[Formula 8]

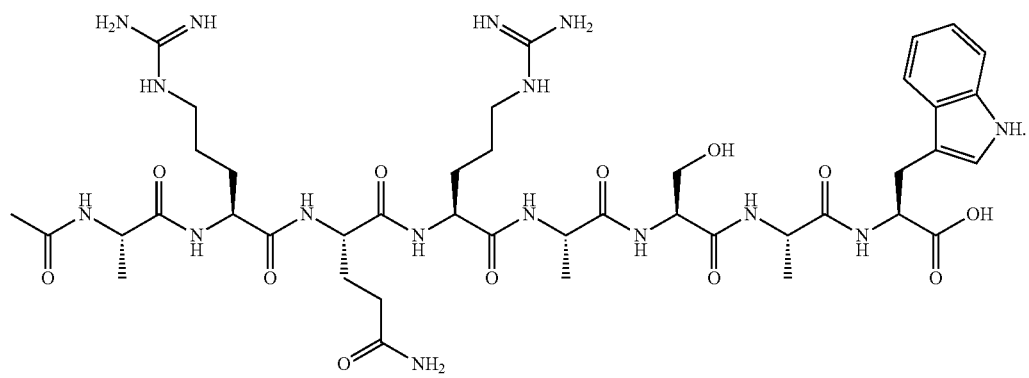

[Formula 9]

3. A method for treating an allergic or asthmatic disease, comprising:
   administering to a subject in need thereof an effective amount of a pharmaceutical composition comprising the peptide derivative of claim 1 or a salt thereof.

4. The method according to claim 3, wherein the peptide derivative of Formula 1 is selected from those represented by Formulae 2 to 9:

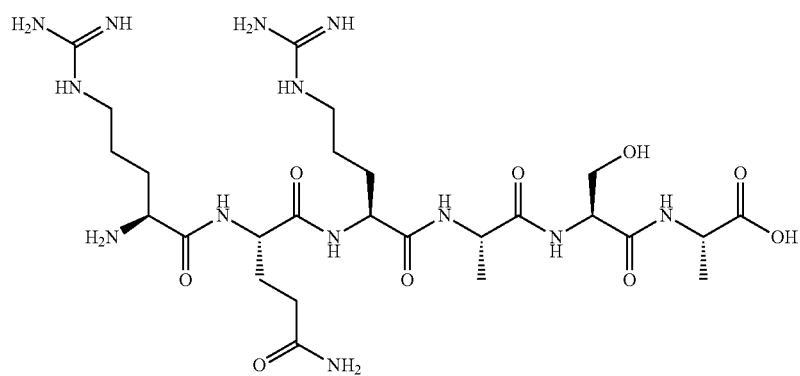

[Formula 2]

[Formula 3]
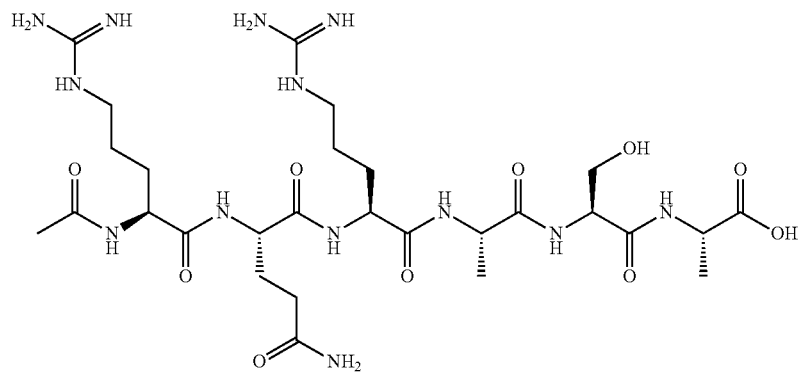
[Formula 4]
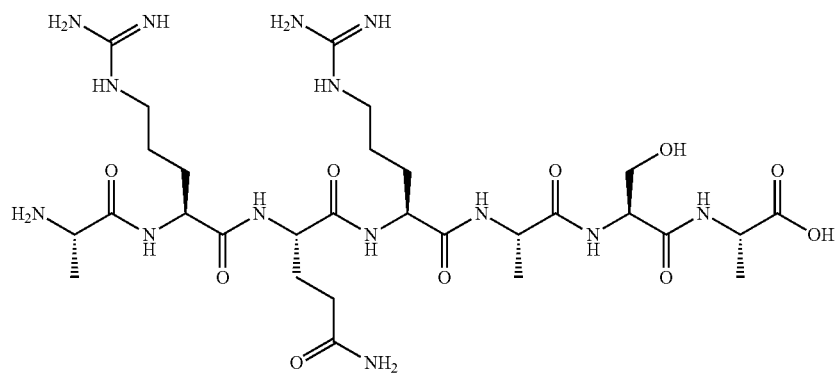
[Formula 5]
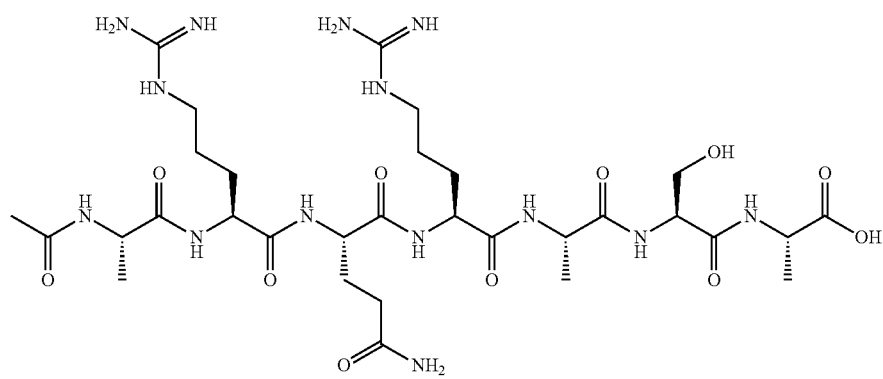
[Formula 6]
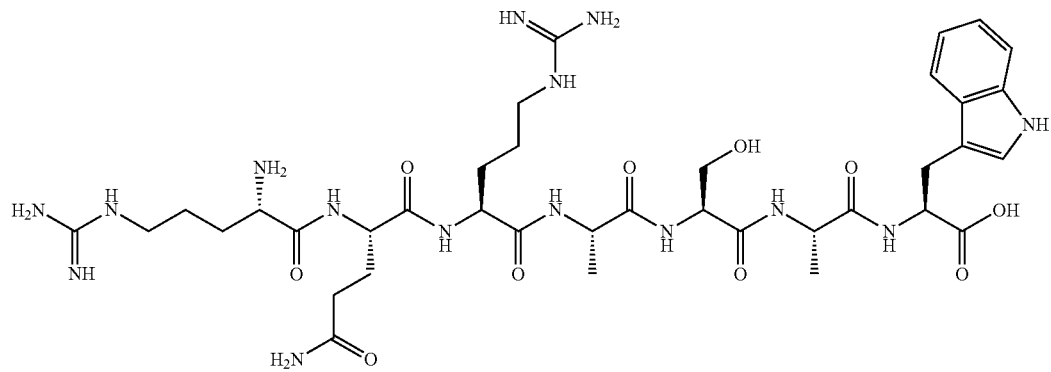

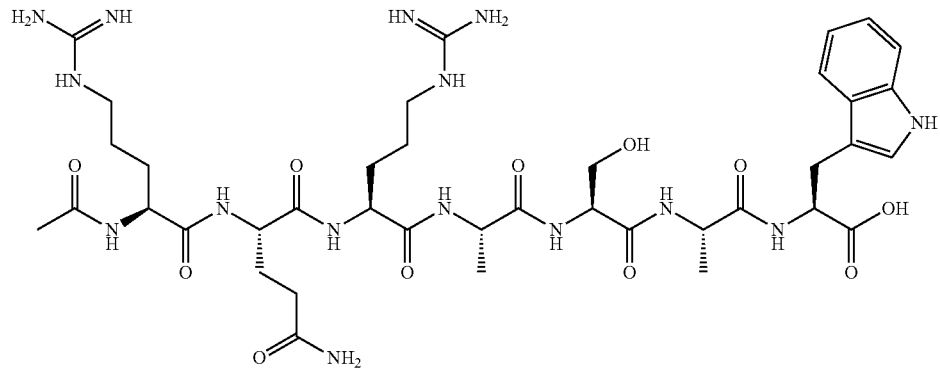

[Formula 7]

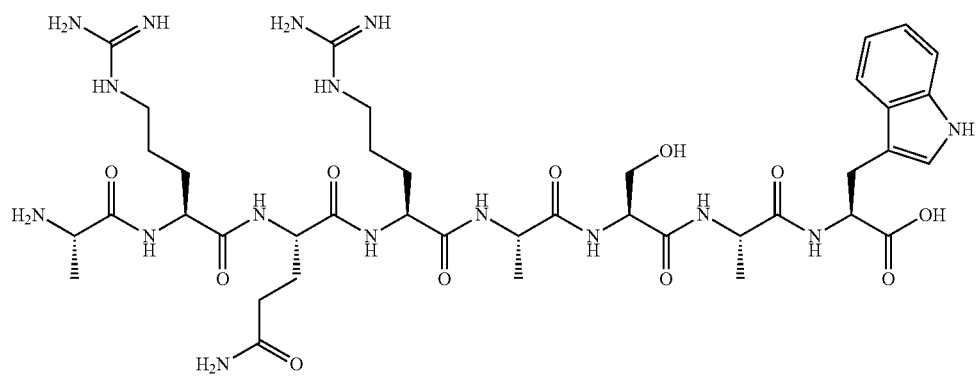

[Formula 8]

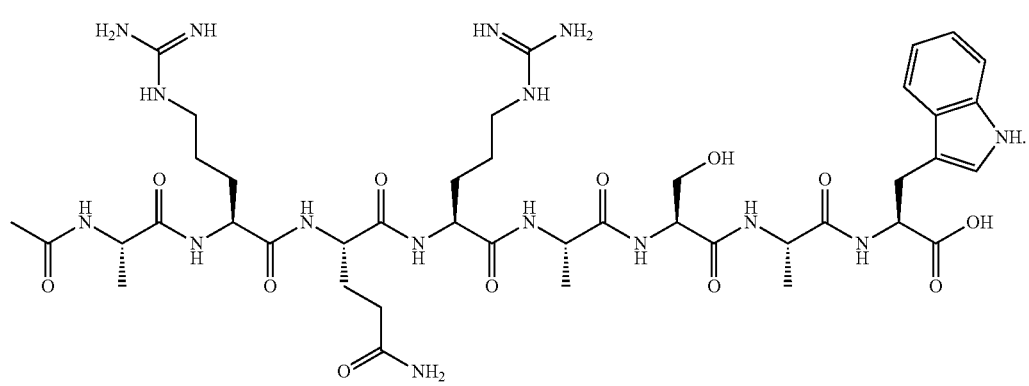

[Formula 9]

5. The method according to claim 3, wherein the allergic disease is selected from the group consisting of atopic dermatitis, rash, and allergic rhinitis.

6. The method according to claim 3, wherein the composition further comprises one or more ingredients selected from the group consisting of other drugs for preventing and treating an allergic or asthmatic disease, excipients, diluents, adjuvants, and stabilizers.

7. The method according to claim 6, wherein the stabilizers are selected from the group consisting of proteins, carbohydrates, buffers, and mixtures thereof.

* * * * *

SEQUENCE LISTING

```
<160> NUMBER OF SEQ ID NOS: 8

<210> SEQ ID NO 1
<211> LENGTH: 6
<212> TYPE: PRT
<213> ORGANISM: Artificial Sequence
<220> FEATURE:
<223> OTHER INFORMATION: TSLP inhibitor

<400> SEQUENCE: 1

Arg Gln Arg Ala Ser Ala
1               5

<210> SEQ ID NO 2
<211> LENGTH: 6
<212> TYPE: PRT
<213> ORGANISM: Artificial Sequence
<220> FEATURE:
<223> OTHER INFORMATION: TSLP Inhibitor
<220> FEATURE:
<221> NAME/KEY: MOD_RES
<222> LOCATION: (1)..(1)
<223> OTHER INFORMATION: ACETYLATION

<400> SEQUENCE: 2

Arg Gln Arg Ala Ser Ala
1               5

<210> SEQ ID NO 3
<211> LENGTH: 7
<212> TYPE: PRT
<213> ORGANISM: Artificial Sequence
<220> FEATURE:
<223> OTHER INFORMATION: TSLP Inhibitor

<400> SEQUENCE: 3

Ala Arg Gln Arg Ala Ser Ala
1               5
```

```
<210> SEQ ID NO 4
<211> LENGTH: 7
<212> TYPE: PRT
<213> ORGANISM: Artificial Sequence
<220> FEATURE:
<223> OTHER INFORMATION: TSLP Inhibitor
<220> FEATURE:
<221> NAME/KEY: MOD_RES
<222> LOCATION: (1)..(1)
<223> OTHER INFORMATION: ACETYLATION

<400> SEQUENCE: 4

Ala Arg Gln Arg Ala Ser Ala
1               5

<210> SEQ ID NO 5
<211> LENGTH: 7
<212> TYPE: PRT
<213> ORGANISM: Artificial Sequence
<220> FEATURE:
<223> OTHER INFORMATION: TSLP Inhibitor

<400> SEQUENCE: 5

Arg Gln Arg Ala Ser Ala Trp
1               5

<210> SEQ ID NO 6
<211> LENGTH: 7
<212> TYPE: PRT
<213> ORGANISM: Artificial Sequence
<220> FEATURE:
<223> OTHER INFORMATION: TSLP Inhibitor
<220> FEATURE:
<221> NAME/KEY: MOD_RES
<222> LOCATION: (1)..(1)
<223> OTHER INFORMATION: ACETYLATION

<400> SEQUENCE: 6

Arg Gln Arg Ala Ser Ala Trp
1               5

<210> SEQ ID NO 7
<211> LENGTH: 8
<212> TYPE: PRT
<213> ORGANISM: Artificial Sequence
<220> FEATURE:
<223> OTHER INFORMATION: TSLP Inhibitor

<400> SEQUENCE: 7

Ala Arg Gln Arg Ala Ser Ala Trp
1               5

<210> SEQ ID NO 8
<211> LENGTH: 8
<212> TYPE: PRT
<213> ORGANISM: Artificial Sequence
<220> FEATURE:
<223> OTHER INFORMATION: TSLP Inhibitor
<220> FEATURE:
<221> NAME/KEY: MOD_RES
<222> LOCATION: (1)..(1)
<223> OTHER INFORMATION: ACETYLATION

<400> SEQUENCE: 8

Ala Arg Gln Arg Ala Ser Ala Trp
1               5
```